United States Patent [19]
Longstreth et al.

[11] Patent Number: 5,955,500
[45] Date of Patent: Sep. 21, 1999

[54] PHARMACEUTICAL COMPOSITIONS CONTAINING NON-RACEMIC VERAPAMIL AND PROCESS FOR OPTIMIZING THE PHARMACEUTICAL ACTIVITY OF R- AND S-VERAPAMIL

[75] Inventors: James A. Longstreth, Mundelein, Ill.; Jamali Fakhreddin, Edmonton, Canada

[73] Assignee: G. D. Searle & Co., Chicago, Ill.

[21] Appl. No.: 08/863,048

[22] Filed: May 23, 1997

Related U.S. Application Data

[60] Provisional application No. 60/018,176, May 23, 1996.

[51] Int. Cl.$^6$ .............................. A61K 9/54; A61K 9/24; A61K 31/275
[52] U.S. Cl. ............................................................. 514/523
[58] Field of Search ............................................. 514/523

[56] References Cited

U.S. PATENT DOCUMENTS 5,457,224  10/1995  Ehrmann et al. ......................... 253/30

FOREIGN PATENT DOCUMENTS

| | | | |
|---|---|---|---|
| 0270782 | 6/1988 | European Pat. Off. ..... | A61K 31/275 |
| 2598080A1 | 11/1987 | France .......................... | A61K 31/135 |
| 2059923 | 6/1972 | Germany . | |
| 2059985 | 6/1972 | Germany . | |
| WO8700042 | 1/1987 | WIPO .............................. | A61K 9/00 |
| WO9001317A1 | 2/1990 | WIPO .......................... | A61K 31/275 |
| WO9301803A1 | 2/1993 | WIPO .............................. | A61K 9/16 |
| WO 97/33570 | 9/1997 | WIPO . | |

OTHER PUBLICATIONS

Overhead projection presented at *Drug Information Workshop*, Apr. 27–29, (1992), "Stereoselectivity of Thalidomide Toxicity in Mice".
Overhead projection presented at *Drug Information Workshop* Apr. 27–29, (1992), "Generic Applications of Chiral Products".
Presentation by Prof. Tucker, "D) Racemate Used —Isomer Preferable", Data unknown.
Final version, Investigation of Chiral Active Substances, European Commission, 1993.
Karim, A., Drug Information Association Workshop, "Should Plasma Levels of Enantiomers be Determined in Evaluating the Bioavailability of Chiral Drugs?", Apr. 27–29, 1992.
McMahon, G. et al., "The Importance of Chirality to Antihypertensive Drug Effects", *Current Therapeutic Research*, vol. 52, pp. 89–97, 1992.
Kwon, Y. and Triggle, D.J., "Chiral Aspects of Drug Action at Ion Channels: A Commentary on the Stereoselectivity of Drug Actions at Voltage–Gated Ion Channels With Particular Reference to Verapamil Actions at the $Ca^{2+}$ Channel", *Chirality*, 3:393–404 (1991).
Wilson, K. and Walker, J., "Chirality and Its Importance in Drug Development", Biochemical Society Transactions, vol. 19, pp. 443–475, (1991).
Eleventh draft of guidance note from European Commission, CPMP Working Party on Quality of Medicinal Products, CPMP Working Party on Safety of Medicinal Products, CPMP Working Party on Efficacy of Medical Products, Investigation of Chiral Active Substances, Oct. 1992.

*Primary Examiner*—Frederick Krass
*Attorney, Agent, or Firm*—Fitzpatrick, Cella, Harper & Scinto

[57] ABSTRACT

Pharmaceutical compositions containing non-racemic mixtures of verapamil are described, as well as a process of making pharmaceutical compositions containing unequal amounts of R- and S-verapamil.

A process for customizing a pharmaceutical composition containing R-verapamil and S-verapamil to optimize a selected pharmaceutical activity comprises selecting a pharmaceutical activity possessed by R-verapamil or S-verapamil, alone or in combination, and then determining a target plasma level for R-verapamil and S-verapamil to achieve that activity is also described. A dosage form for administering the drug is selected. Based on dosage form, one determines the relative amounts of R- and S-verapamil to incorporate into the dosage form to achieve the targeted plasma levels. The dosage form can then be formulated.

20 Claims, 12 Drawing Sheets

PHARMACEUTICAL COMPOSITIONS CONTAINING NON-RACEMIC VERAPAMIL AND PROCESS FOR OPTIMIZING THE PHARMACEUTICAL ACTIVITY OF R- AND S-VERAPAMIL

RELATED APPLICATIONS

This application claims the benefit of U.S. Provisional Application No. 60/018,176 filed May 23, 1996 by the present inventors.

BACKGROUND OF THE INVENTION

1. Field of the Invention

This invention uses the unequal pharmacological activities (both for toxic events and therapeutic events) and the different pharmacokinetics of the enantiomers of verapamil as a basis for customizing the administered verapamil enantiomer mixture to produce a desired verapamil enantiomer ratio in the plasma or serum of patients.

2. Brief Description of the Prior Art

Verapamil, benzeneacetonitrile, α-[3-[[2-(3,4-dimethoxyphenyl)ethyl]methylamino]propyl]-3,4-dimethoxy-α-(1-methylethyl) hydrochloride, is a commercially available drug. It is a calcium ion influx inhibitor (slow channel blocker or calcium ion antagonist).

Current marketed verapamil dosage forms intended for cardiovascular therapy contain equal amounts of R-verapamil and S-verapamil. When administered intravenously this mixture produces circulating R-verapamil concentrations that are approximately twice the S-verapamil concentrations. When administered orally as an immediate release formulation, this mixture produces approximately a 3:1 R:S ratio in the systemic circulation; as an oral sustained release formulation the plasma ratio is approximately 5:1. Thus a single chemical composition produces chemically dissimilar plasma concentrations, and pharmacologically dissimilar effects depending on the route of administration, and the type of formulation used.

It is an object of the present invention to provide consistent dosage effects by tailoring the enantiomeric composition (i.e., the enantiomeric ratio) of the administered dosage form to the route of administration and/or the rate of drug release.

It is another object of the present invention to manipulate the enantiomeric ratio of the administered drug based on formulation and route of administration to yield systemic plasma enantiomer concentration ratios that are associated with desired risk-benefit ratios for a targeted indication.

SUMMARY OF THE INVENTION

These objects and others are attained by the present invention, which provides administered dosage forms with a specific approximate enantiomer ratio taking into account two phenomena: (1) the balance of desirable R- and S-verapamil therapeutic activities, and acceptable R- and S-verapamil adverse activities for the targeted indication (the balance will differ depending on whether anti-anginal effects or antihypertensive effects are most important); and (2) the differential distribution, metabolism and excretion pharmacokinetics of the two enantiomers.

This invention takes advantage of the well-known stereospecific pharmacokinetic and pharmacodynamic behaviors of verapamil. Previous to this invention, one sought the "safest" dosage formulation that could be produced containing a racemic mixture of the verapamil enantiomers. This invention now allows the identification of a known safe and beneficial enantiomeric combination in the systemic circulation of patients, to be translated into one or more dosage formulations, depending on the desired route of administration and dosage form release rate.

DETAILED DESCRIPTION OF THE INVENTION

Figure 1:
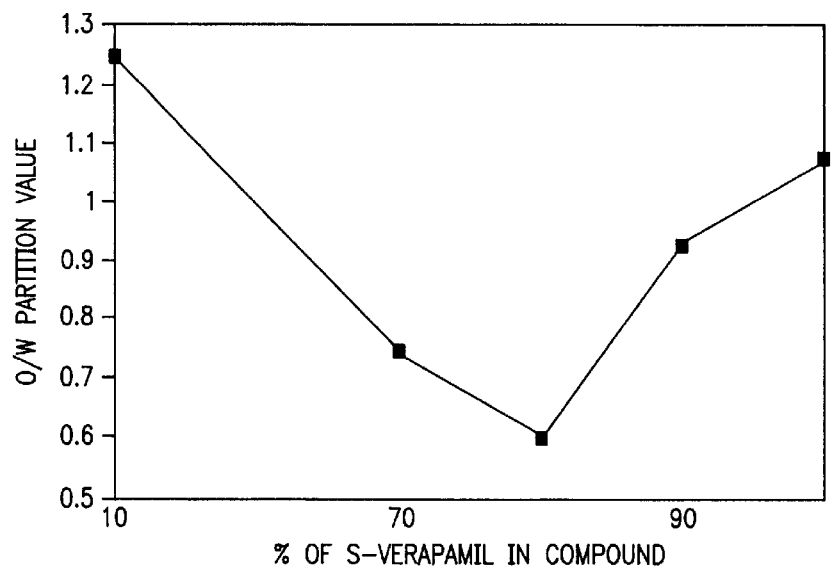
FIG. 1 is a phase diagram of racemic verapamil based on octanol/water partition coefficient at pH 5.

The enantiomers of verapamil have long been known to have unequal pharmacological potencies for their dromotropic (S=10×R), inotropic (S=15–50×R), chronotropic (S=3×R) and vasodilatory (S=2–3×R) activities on the cardiovascular system. However, they have also been shown to be equipotent (S=R) at inhibiting the transport system responsible for multiple drug resistance (MDR). The pharmacokinetic differences range from differences in the volume of distribution (S=2×R) and protein binding (S=94%, R=88%) to differences in the Michaelis-Menton parameters associated with hepatic metabolism. This invention exploits the pharmacokinetic differences between the two verapamil enantiomers to generate a ratio of the enantiomers in the circulating plasma that can create a desired balance of therapeutic and toxic activities.

For example, one range of plasma ratios (R>S) can be targeted to produce the maximum possible antihypertensive effect and minimum possible cardiac conduction effect. A different range, using a larger fraction of S can be targeted to produce the maximum antihypertensive effect and minimum possible impact on heart rate. A third range can be targeted to produce the maximal antihypertensive activity and minimal constipative (gut motility) effect. Yet another set of ranges e.g. (S>R) can be targeted to obtain maximal anti-anginal effects for an acceptable level of adverse events (slowing of cardiac conduction, alteration in heart rate, slowed gut motility).

The ratios sought above can only be obtained by taking into consideration the different pharmacokinetics of the two enantiomers and the route of administration. For example, if an approximately 8:1 (R:S) ratio in the plasma is desired for maximum antihypertensive activity and minimum increase in heart rate, then the ratio of enantiomers in an intravenous injection or infusion would have to be approximately 8:2. If the drug was being administered orally as an immediate release formulation, then the formulation would need to contain the enantiomers in an approximately 8:3 ratio. If the drug was being administered orally as a sustained release formulation, then the formulation would need to contain the enantiomers in an approximately 8:5 ratio.

Previous use of the 1:1 enantiomer ratio in a racemic dosage form is an uncontrolled byproduct of the manufacturing/synthesis process, not the result of conscious design. Similarly, prior use of a single enantiomer drug product is the result of a decision that all, or most, of the desired activity lies with one of the enantiomers, and all, or most, of the undesired activities are associated with the other enantiomer. This does not represent a balancing of the positive and negative properties, both being associated to (potentially) different extents with both enantiomers. The single enantiomer version of verapamil (R-verapamil) for use in reducing MDR, is a selection based on its lesser potency for negative dromotropic activities.

Minimization of side effects is a standard selection criterion for selection between and among possible development candidates. Manipulating the enantiomeric ratio to produce the desired balance of therapeutic and adverse effects is a new and novel approach.

Thus, the present invention includes a process for customizing a pharmaceutical composition containing R-verapamil and S-verapamil to optimize a selected pharmaceutical activity. The process comprises selecting a pharmaceutical activity possessed by R-verapamil or S-verapamil, alone or in combination, and then determining a target plasma level for R-verapamil and S-verapamil to achieve that activity. A dosage form for administering the drug is selected. Based on dosage form, one determines the relative amounts of R- and S-verapamil to incorporate into the dosage form to achieve the targeted plasma levels. The dosage form is then formulated.

Pharmaceutical compositions containing non-racemic mixtures of verapamil are a part of this invention, as well as a process of making pharmaceutical compositions containing unequal amounts of R- and S-verapamil.

EXAMPLE 1

Stereochemically pure enantiomers of verapamil HCl were obtained from RBI Research Biochemical Inc. (Natick, Mass.) to construct a phase diagram for S-verapamil in the presence of R-verapamil and examine whether the physicochemical properties of the resulting compounds depend on the S:R ratio.

Exact amounts of the enantiomers were carefully weighed and mixed to prepare compounds consisting of 50, 70, 80, 90 and 100% of S-verapamil and sufficient amount of R-verapamil to make 100%.

The melting points of the stereochemically pure and racemic verapamil were measured without crystallization. However, to allow complete interaction of the enantiomers, the compounds were dissolved in HPLC water and then, in an attempt to solidify the residue for determination of melting point, the solutions were evaporated under vacuum. The melting point was determined using a Uni-Melt Thomas Hoover capillary melting point apparatus.

In a 10 mL screw cap glass tube (n=3 for each), 100 $\mu$L of solutions containing 100 $\mu$g/mL of compounds in water, and 900 $\mu$L of phosphate buffer (pH, 5, 6 and 7.4) were mixed and 1 mL of analytical grade 1-octanol (Fisher Scientific, Edmonton, Canada) was added. The tubes were capped, vortex-mixed, placed in a 27° water bath and were shaken for a predetermined time of 3 hours. The concentration of the verapamil compounds in both aqueous and octanol layer were determined using a non-stereospecific assay.

The verapamil content of the samples was determined using a HPLC method: To 100 $\mu$L of the aqueous layer were added 50 $\mu$L of internal standard (50 $\mu$g/mL ibuprofen in 0.001 M NaOH) and 100 $\mu$L of mobile phase. The resulting solutions were injected into HPLC. For the measurement of the drug in the octanol phase, the content of 0.5 mL of the sample were added 0.3 mL of HPLC water and 0.2 mL of 0.25 M HCl. After vortex-mixing the mixture, the verapamil content was completely extracted to the aqueous layer. The aqueous layer was then subjected to the sample preparation as described above. The verapamil concentration was determined against standard curves prepared under the same conditions.

| HFLC Conditions: | |
|---|---|
| Column | ODS-3 reversed phase Whatman $C_{18}$ 5 microns 10 cm steel column. |
| Mobile phase | Acetonitrile/water/acetic acid/triethylamine (46.5:53.5:0.1:0.03), flow, |

-continued

| HFLC Conditions: | |
|---|---|
| | 1 mL/min |
| Detector | Waters model 481 at 232 nm |
| Pump | Waters model M45 |
| Autosampler | Waters Wisp model 710B |
| Integrator | Hewlett-Packard Model 3390A |
| Internal Standard | Racemic ibuprofen |
| Linearity | from 0.5–40 µg/mL |
| CV % | <6.2% |

Racemic, S- and R-verapamil melted with decomposition at 144±0.82, 132±0.82 and 132±1.25°, respectively.

To allow interaction between molecules of the enantiomers, the prepared compounds with various ratios of S- and R-verapamil were dissolved in water and then attempts were made to recrystallize the compounds for measurement of the melting point. The prepared compounds, however, did not solidify. Alternatively, a phase diagram was prepared based on the partition coefficient ($P_{o/w}$) rather than melting point as depicted in FIG. 1 and Table I.

The $P_{o/w}$ could not be accurately measured at pH values of 6 and 7.45 as almost the entire amount of the drug was extracted into the octanol layer and consequently the concentration in the buffer layer fell below the assay sensitivity. Alternatively, the phase diagram was constructed at pH 5.

The partition coefficient of verapamil was indeed a function of the S:R ratio. However, racemic and stereochemically pure enantiomers possess very similar $P_{o/w}$ (1.23±0.07 versus 1.08±0.18). Interestingly, however, the compound consisting of 80% S and 20% of R had a very low $P_{o/w}$ (0.60±0.05) and was identified as the eutectic compound.

Distribution of drugs in the body are controlled by factors such as their partition coefficient. This property may influence the amount of the drug which enters various tissues to elicit desirable or untoward effects. It is clear from the data that the verapamil partition coefficient is indeed a function of the enantiomers ratio. The existence of a eutectic point is important as the properties of the drug at this particular S:R ratio may be different from any other composition. For example, due to its very low partition coefficient, the eutectic compound may have a smaller extent of distribution in the body which may have significant therapeutic outcomes.

Verapamil is highly bound to plasma proteins in a stereoselective fashion. Hence, after administration of verapamil, a eutectic point is only achieved when the unbound (rather than total) verapamil concentration is comprised of an 80:20 ratio.

TABLE 1

Partition Coefficient of Verapamil Compound at pH 5

| Compound | Concentration µg/mL | | $P_{o/w}$ |
|---|---|---|---|
| % of S in R | in octanol | in water | O/W |
| 50 | 6.02 | 5.05 | 1.19 |
| 50 | 6.36 | 4.80 | 1.33 |
| 50 | 5.83 | 4.75 | 1.23 |
| 50 | | Mean $P_{o/w}$ ± SD, 1.25 ± 0.07 | |
| 70 | 4.35 | 5.81 | 0.75 |
| 70 | 4.20 | 6.00 | 0.70 |
| 70 | 4.24 | 5.38 | 0.79 |
| 70 | | Mean $P_{o/w}$ ± SD, 0.75 ± 0.05 | |
| 80 | 4.16 | 6.95 | 0.60 |
| 80 | 4.49 | 6.93 | 0.65 |
| 80 | 3.81 | 6.92 | 0.55 |
| 80 | | Mean $P_{o/w}$ ± SD, 0.60 ± 0.05 | |
| 90 | 5.80 | 5.90 | 0.98 |
| 90 | 5.29 | 6.18 | 0.86 |
| 90 | 4.79 | 5.10 | 0.94 |
| 90 | | Mean $P_{o/w}$ ± SD, 0.93 ± 0.06 | |
| 100 | 5.53 | 6.22 | 0.89 |
| 100 | 5.15 | 4.08 | 1.26 |
| 100 | 5.29 | 4.88 | 1.08 |
| 100 | | Mean $P_{o/w}$ ± SD, 1.08 ± 0.18 | |

EXAMPLE 2

Improvement in cardiac function in patients with coronary artery disease, in those experiencing angina, or those recovering from an infarct is achieved, in many instances, by appropriate drug therapy. A number of confounding factors, however, including the concentration of the drug used and the fact that certain enantiomers of optically active drugs have different pharmacokinetic properties often make it confusing for the clinician to establish a clear course of therapeutic action for the coronary care patient. See Jamali, F. et al. 1991. Enantioselective aspects of drug action and disposition: Therapeutic pitfalls. J. of Pharmaceutical Sciences 78(9): 695–715 and Heijnis, J. B. et al., 1991. Effects of various calcium antagonists in isolated perfused hearts from diabetic and age matched control rats. J. Cardiov. Pharmacol. 17(6) 983–19.

A series of experiments was conducted on the isolated working rat heart preparation of Neely as published in Neely, J. R. and M. J. Rovetto, 1975. Techniques for perfusing hearts. Methods Enzymo. 39: 43–60. These experiments address some of enantioselective effects as well as the effects of variable R/S ratios of verapamil on cardiac function.

According to the Neely method of heart perfusions, hearts were excised from Na pentobarbital anesthetized Sprague-Dawley male rats (250–350 g) and placed in ice cold buffer, then quickly cannulated as Langendorff (nonworking) or Neely (working) hearts. Heart perfusions were initiated with Krebs-Henseliet buffer, pH 7.4, gassed with 95% $O_2$ and 5% $CO_2$ containing 2.5 mM free calcium and 11 mM glucose. When switched to the working mode, the hearts were perfused with buffer containing 4.9 mM K+ and 3% bovine serum albumin in the presence of 0.4 mM palmitate. The working heart buffer had previously been dialyzed (16 hours) against 10 vol. Krebs-Henseliet buffer (NaCl, 121 mM, KCl 3.7 mM, $KH_2PO_4$ 1.2 mM, $MgSO_4$-$7H_2O$ 1.2 mM, $CaCl_2$-$2H_2O$ 3.0 mM). The working hearts were perfused with recirculated buffer (100 ml) at a left atrial filling pressure of 11.5 mm Hg and hydrostatic after load of 60 mm Hg. Langendorff (nonworking hearts) were perfused at a constant pressure of 100 cm $H_2O$.

Drugs, when used, were added as single components or mixtures. In this study S-verapamil-HCl and R-verapamil-HCl were added directly to the perfusate reservoir. They were prepared and analyzed in our laboratory according to the method of Jamali, cited above. Stock solutions (10 mg/100 ml) of the drugs were made in HPLC-$H_2O$.

All working hearts were initially subjected to 20 min. aerobic perfusion during which heart rate (HR), peak systolic pressure (PSP), cardiac function (as Rate-Pressure Product, RPP), and cardiac output (CO) stabilized. HR and PSP were recorded continuously throughout each experiment via a fluid filled sidearm on the aortic cannula connected to a pressure transducer. The pressure transducer was connected to a Beckman Type R Dynograph supplied with a type 9853 strain gauge coupler and a type 9857 cardiotachometer coupler. Cardiac output was determined by collecting perfusate for a period of 15 sec. through a "T" connector placed in the afterload line 40 cm above the heart. After measuring the volume of perfusate collected, it was poured back into the reservoir. Occasionally, coronary flow was determined by collecting perfusate drip from the pulmonary artery.

Initially, a concentration-effect curve for racemate verapamil on heart rate was established. Beginning at a concentration of $10^{-7}$ M with a stepwise increase up to $10^{-5}$ M, HR and PSP recordings were made. The effect of the drug on these indices was observed for 5 min. at each concentration used and recordings made.

Additional experiments to determine the effects of single enantiomers and/or ratios of enantiomers on cardiac function were then completed. Total perfusion time for each working heart preparation, including stabilization plus verapamil addition(s) amounted to approximately 2 hr. Throughout each experiment, at predetermined intervals (2–15 min.), HR, PSP, RPP, and CO were determined.

Throughout these experiments the perfusate concentrations of verapamil used were: S, 100 ng/ml; R, 50, 200, 450 and 950 ng/ml, with corresponding R/S ratios of 0.5, 2.0, 4.5 and 9.5, respectively. In all experiments, heart rate, peak systolic pressure, cardiac function and cardiac output were determined at selected intervals before and after administration of verapamil. The following series of experiments were conducted and comparisons made:

1. The effects of R and S verapamil alone, or together (FIG. 2).
2. The effects of a gradual increase in R to the recirculating perfusate containing an initial dose of S (FIG. 3).
3. The effects of a gradual increase in R (FIG. 4).

In the first group of experiments, the effect of R and S verapamil alone, or together, were compared on the following: heart rate, peak systolic pressure, cardiac function and cardiac output.

Figure 2A:
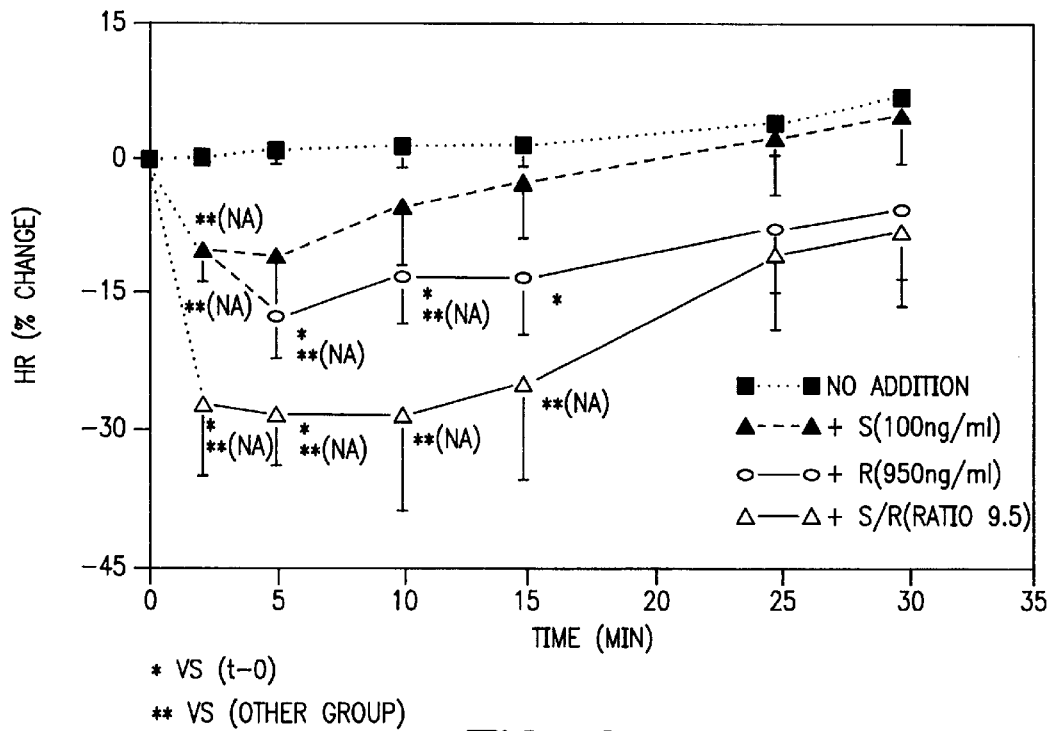
FIG. 2a illustrates changes in heart rate in isolated working rat heart following addition of R-, S- or a 950/100 ratio of R-/S-verapamil to the recirculating perfusate.

The data obtained for the heart rate measurements using R and S verapamil alone and in a 9.5 R/S ratio were plotted as a percent of baseline values determined during the pre-drug stabilization period, and are graphically represented in FIG. 2a.

Figure 2B:
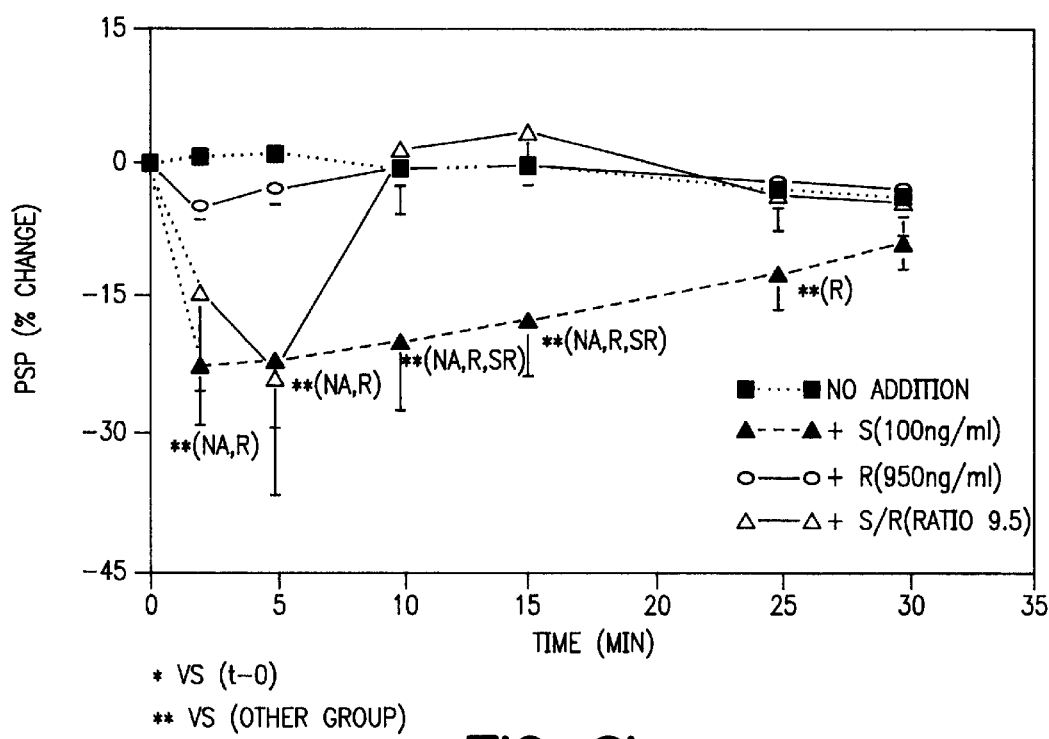
FIG. 2b illustrates changes in peak systolic pressure in isolated working rat heart following addition of R-, S- or a 950/100 ratio of R-/S-verapamil to recirculating perfusate.

The data obtained for peak systolic pressure using R and S verapamil alone and in a 9.5 R/S ratio were plotted as a percent of baseline values determined during the pre-drug stabilization period, and are graphically represented in FIG. 2b.

Figure 2C:
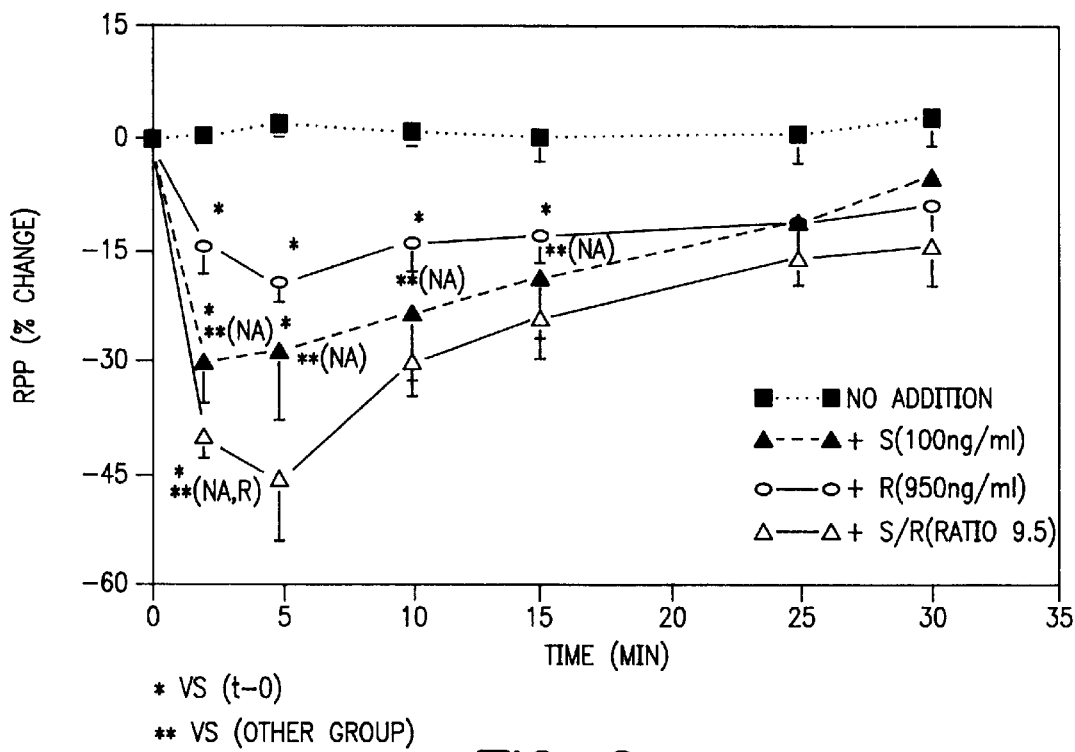
FIG. 2c illustrates changes in cardiac function in isolated working rat heart following addition of R-, S- or a 950/100 ratio of R-/S-verapamil to recirculating perfusate.

The data obtained for the cardiac function measurements (RPP, the rate pressure product) using R and S verapamil alone and in a 9.5 R/S ratio were plotted as a percent of baseline values attained during the pre-drug stabilization period, and are graphically represented in FIG. 2c.

Figure 2D:
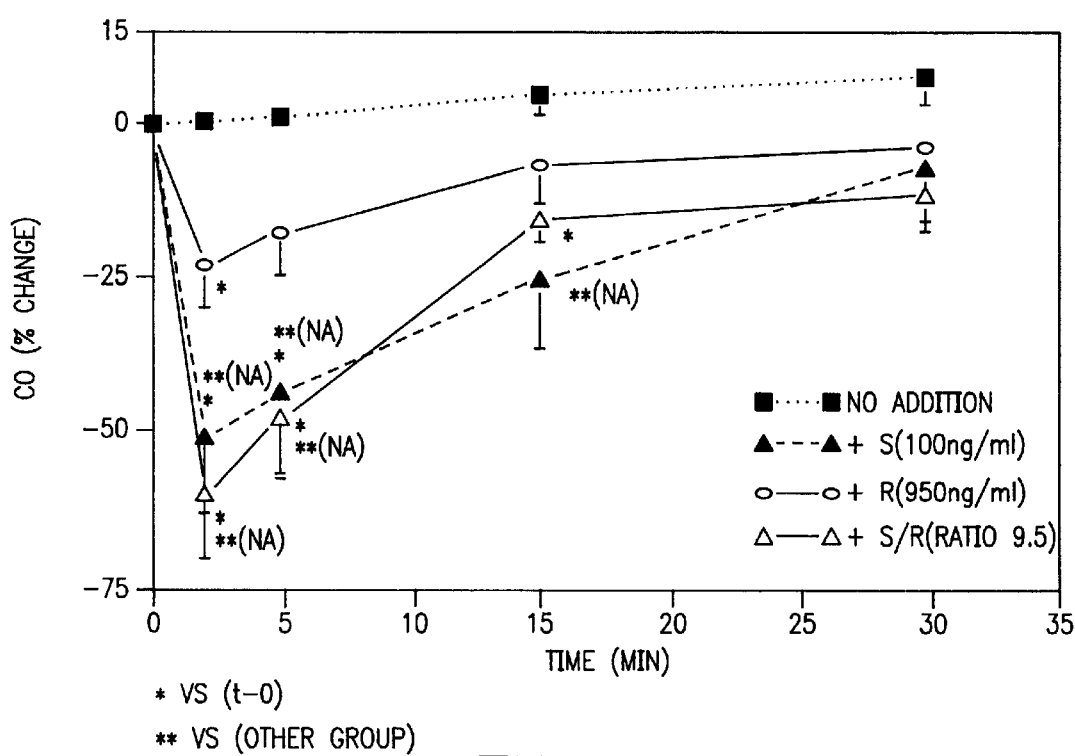
FIG. 2d illustrates changes in cardiac output in isolated working rat heart following addition of R-, S- or a 950/100 ratio of R-/S-verapamil to recirculating perfusate.

The data obtained from the cardiac output measurements for R and S verapamil alone and in a 9.5 R/S ratio were plotted as a percent of baseline values determined during the pre-drug stabilization period, and are graphically represented in FIG. 2d.

TABLE 2

| Indices | Summary | | | |
| --- | --- | --- | --- | --- |
|  | HR | PSP | RPP | CO |
| S 100 ng/ml | n.s. | * | * | * |
| R 950 ng/ml | * | n.s. | * | * |
| R/S ratio (9.5) | * | n.s. | * | * |

*significantly different from pre-drug values

These results show that S-verapamil (100 ng/ml) is primarily an inotropic drug (FIG. 2b) while R-verapamil (950 ng/ml) is primarily chronotropic (FIG. 2a). Evidently S is more effective at reducing peak systolic pressure (FIG. 2b) as well as cardiac output (FIG. 2d). This indicates that S is functioning as a $Ca^{2+}$ channel blocker (i.e. reducing contractility and cardiac output). Following 30 min. perfusion (FIGS. 2a–d), most of the indices measured have returned to pre-drug values. This suggests that the heart may be metabolizing the drugs and/or enhanced binding has occurred, and/or there is receptor tolerance to the drug action.

The effect of the verapamil mixture (R/S ratio: 9.5) on heart rate appears to be additive (FIG. 2a). In contrast, the effect on PSP is not as evident as R (950 ng/ml) appears to suppress the S-induced reduction in PSP (FIG. 2b). Since R, by itself, has no apparent effect on PSP (FIG. 2b), this suggests the enantiomers are not competing for the same receptors and that interaction of the enantiomers has modified membrane stability, thereby suppressing the S-induced reduction in PSP.

EXAMPLE 3

This experiment compares the cumulative effects of R verapamil and various R/S ratios on: heart rate, peak systolic pressure, cardiac function as rate-pressure product (RPP) and cardiac output.

Heart rate changes in the isolated working rat heart following addition of S-verapamil (100 ng/ml) at time "0" and R at +30, +45, +60, and +75 min., respectively were measured. Cumulative concentration of R in the perfusate was 50, 200, 450, and 950 ng/ml, respectively. Values (mean±s.e.m) indicate % change from baseline values established during the initial stabilization period. n=a minimum of 5 hearts.

Heart rate changes in the isolated working rat heart preceding and following addition of R-verapamil at +30, +45, +60, and +75 min., respectively were also measured. Cumulative concentration of R in the perfusate was 50, 200, 450, and 950 ng/ml, respectively. Values (mean±s.e.m) indicate % change from baseline values established during the initial stabilization period. n=a minimum of 5 hearts.

Figure 3A:
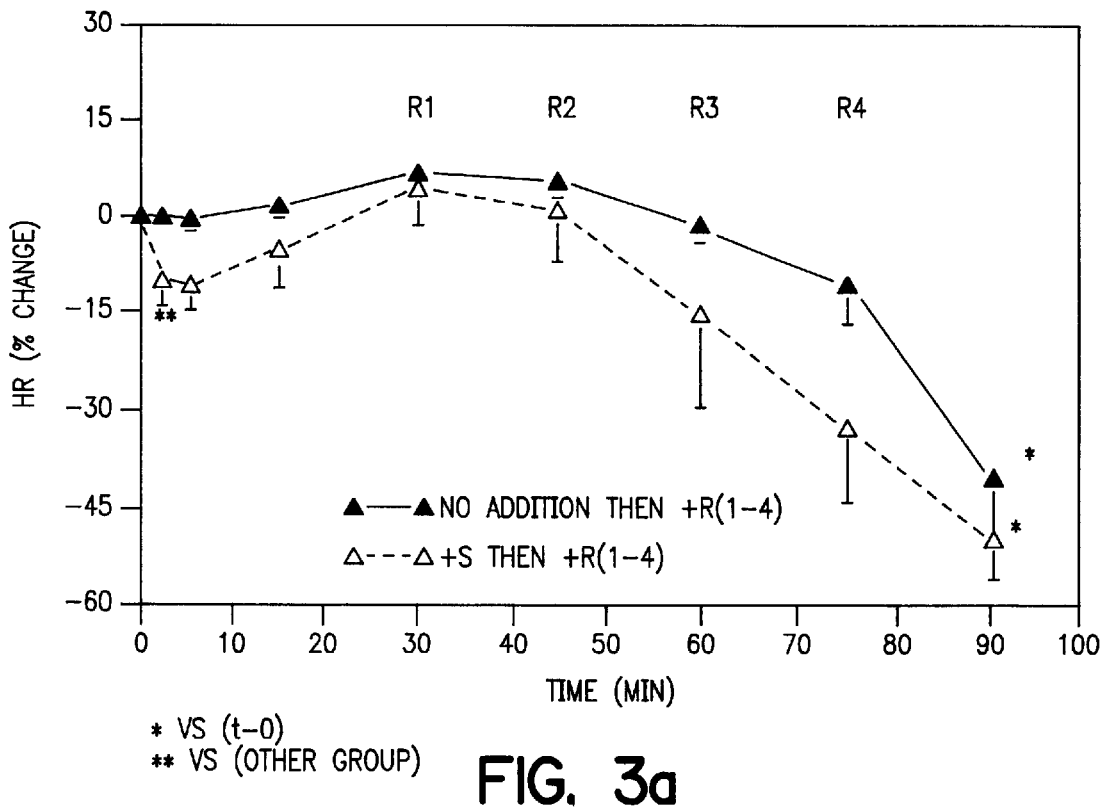
FIG. 3a illustrates changes in heart rate in isolated working rat heart following addition of S-verapamil followed by gradual addition of R-verapamil to the recirculating perfusate.

The data obtained from the above-described experiment were plotted as a percent of baseline values determined during the pre-drug stabilization period, and are graphically represented in FIG. 3a.

Figure 3B:
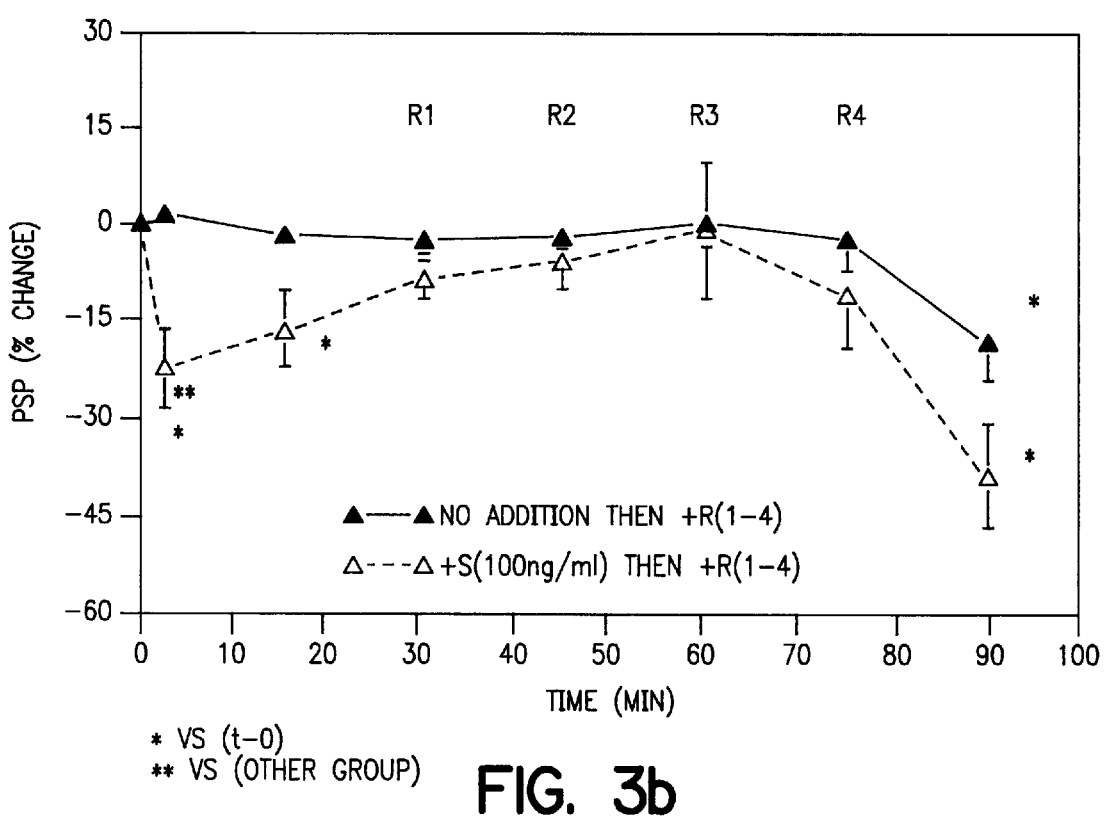
FIG. 3b illustrates changes in peak systolic pressure in isolated working rat heart following addition of S-verapamil followed by gradual addition of R-verapamil to recirculating perfusate.

Using the methodology referred to above, the data from measurements of peak systolic pressure using R-verapamil alone and varying ratios of R- and S-verapamil were plotted as a percent of baseline values determined during the pre-drug stabilization period, and are graphically represented in FIG. 3b.

Figure 3C:
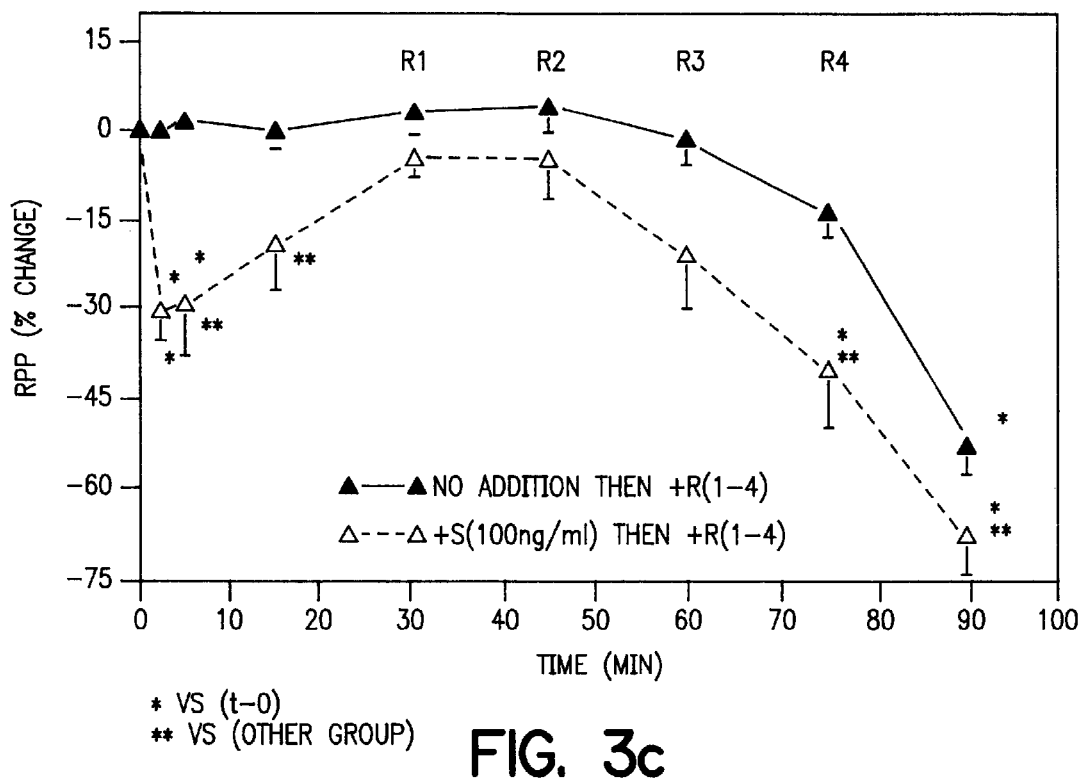
FIG. 3c illustrates changes in cardiac function in isolated working rat heart following addition of S-verapamil followed by gradual addition of R-verapamil to recirculating perfusate.

Using the same methodology, the data from measurements of changes in cardiac function (RPP) using R-verapamil alone and varying ratios of R- and S-verapamil were plotted as a percent of baseline values determined during the pre-drug stabilization period, and are graphically represented in FIG. 3c.

Figure 3D:
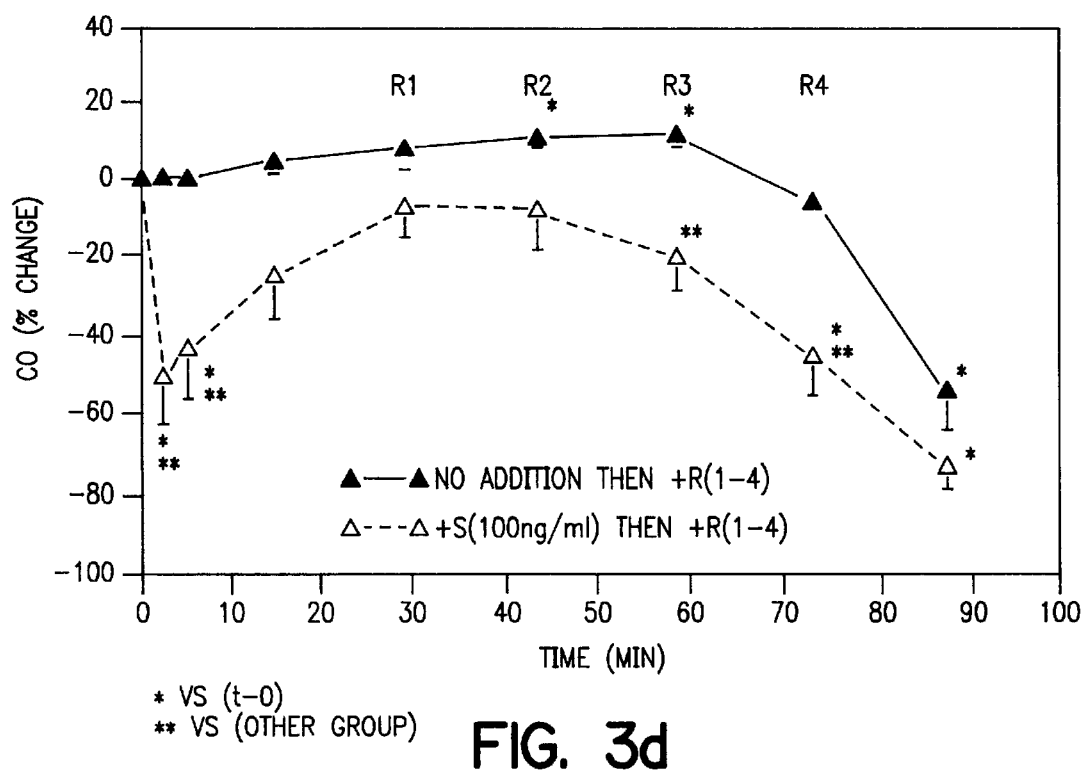
FIG. 3d illustrates changes in cardiac output in isolated working rat heart following addition of S-verapamil followed by gradual addition of R-verapamil to recirculating perfusate.

Using the methodology discussed above, the data from measurements of cardiac output changes using R-verapamil alone and varying ratios of R- and S-verapamil were plotted as a percent of baseline values determined during the pre-drug stabilization period, and are graphically represented in FIG. 3d.

TABLE 3

Summary

| Indices | HR | PSP | RPP | CO |
|---|---|---|---|---|
| R1–R4 | *R4 | n.s. | *R4 | *R2,R3,R4 |
| R/S (0.5) | n.s. | n.s. | n.s. | n.s. |
| R/S (2.0) | n.s. | n.s. | n.s. | n.s. |
| R/S (4.5) | n.s. | n.s. | * | * |
| R/S (9.5) | * | * | * | * |

*significantly different from pre-drug values

Cardiac output appears to increase as the concentration of R exceeds values >200 ng/ml (R2). This increase is slight, however, (FIG. 3d) and must be due to some factor other than an R-induced increase in HR or PSP (FIG. 3a, FIG. 3b). The inventors believe that R has modified membrane integrity thereby affecting $Ca^{2+}$ uptake and/or interaction with contractile proteins. As the R/S ratio exceeds values of 4.5, cardiac function (RPP) is suppressed (FIG. 3c). This response is likely due to the cumulative effect of R on heart rate (FIG. 3a) and/or competition of the enantiomers for similar binding sites on albumin or other receptors. This competition for similar receptors could increase the amount of free S available to the heart for blocking $Ca^{2+}$ channels. The observation that cardiac output (CO) is reduced by approximately 45% at this R/S ratio would support a drug-induced decrease in myocardial contractility at this time.

EXAMPLE 4

This experiment compares the cumulative effects of R-verapamil on: heart rate, peak systolic pressure, cardiac function (RPP) and cardiac output.

The percent change in heart rate during perfusion of the isolated working rat heart was measured. Values (mean±s.e.m) indicate % change from baseline values attained during the initial stabilization period. n=a minimum of 5 hearts.

Heart rate changes in the isolated working rat heart following addition of R verapamil at time "0", +15, +30 and +45, min., respectively were also measured. Cumulative concentration of R in the perfusate was 50, 200, 450, and 950 ng/ml, respectively. Values (mean±s.e.m) indicate % change from baseline values established during the initial stabilization period. n=a minimum of 5 hearts.

Figure 4A:
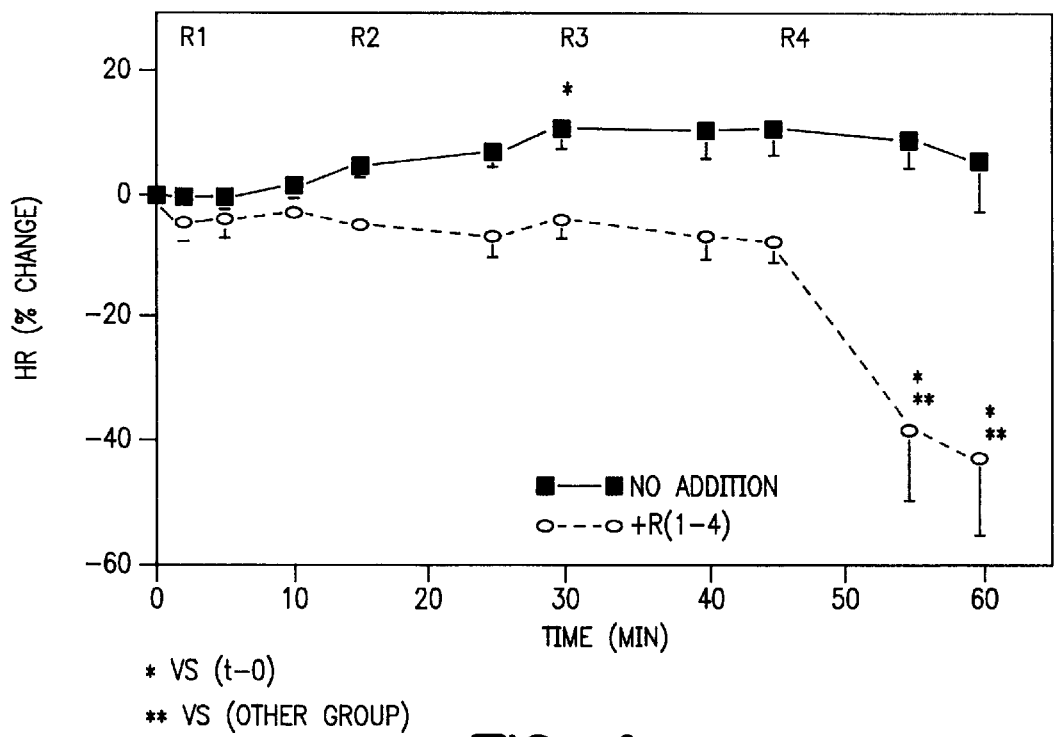
FIG. 4a illustrates changes in heart rate in isolated working rat heart following gradual addition of R-verapamil to the recirculating perfusate.

The data from these experiments measuring heart rate changes using varying amounts of R-verapamil were plotted as a percent of baseline values determined during the pre-drug stabilization period, and are graphically represented in FIG. 4a.

Figure 4B:
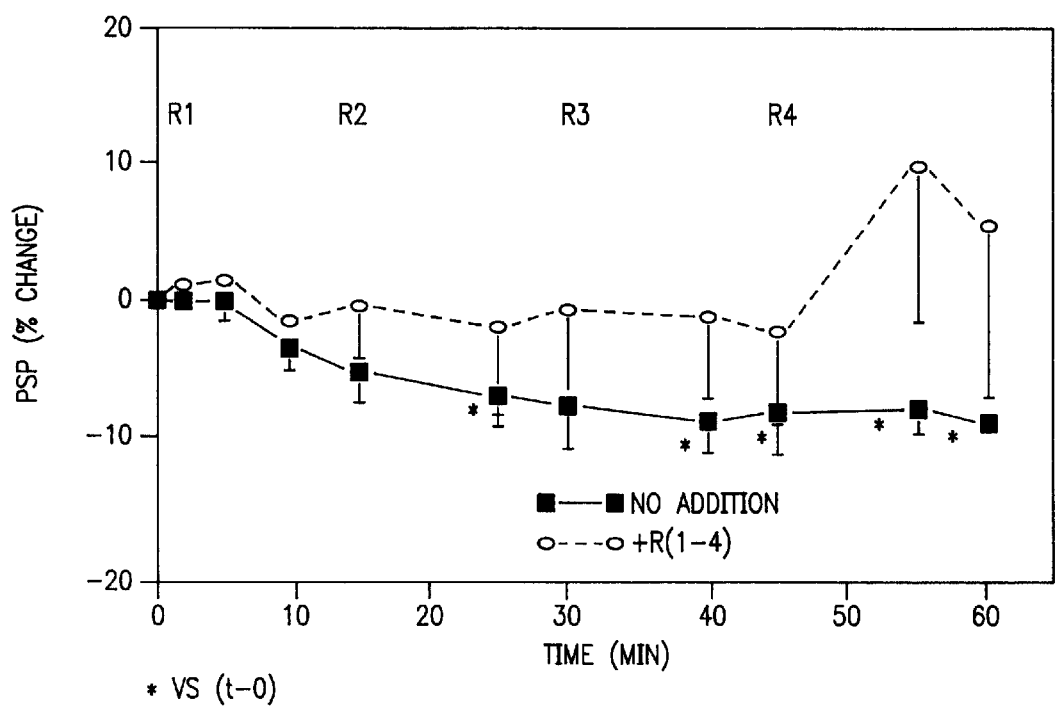
FIG. 4b illustrates changes in peak systolic pressure in isolated working rat heart following gradual addition of R-verapamil to recirculating perfusate.

Using the same methodology, the data obtained on peak systolic pressure changes using varying amounts of R-verapamil were plotted as a percent of baseline values determined during the pre-drug stabilization period, and are graphically represented in FIG. 4b.

Figure 4C:
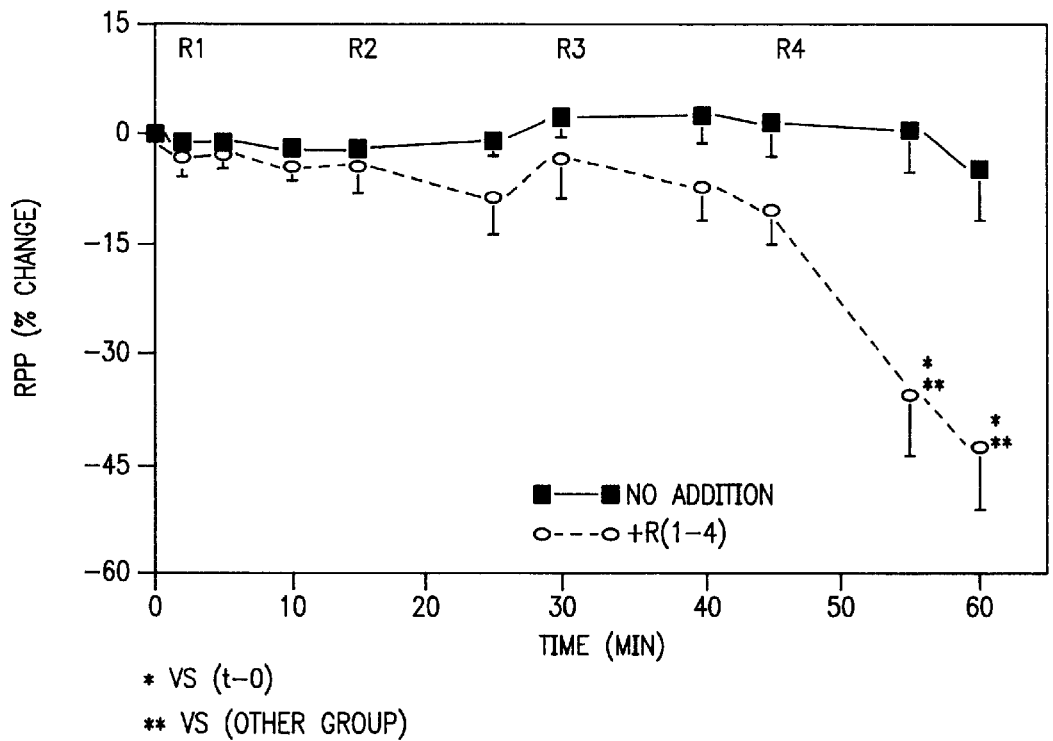
FIG. 4c illustrates changes in cardiac function in isolated working rat heart following gradual addition of R-verapamil to recirculating perfusate.

Using the methodology described above, the data obtained showing changes in cardiac function (RPP) using varying amounts of R-verapamil were plotted as a percent of baseline values determined during the pre-drug stabilization period, and are graphically represented in FIG. 4c.

Figure 4D:
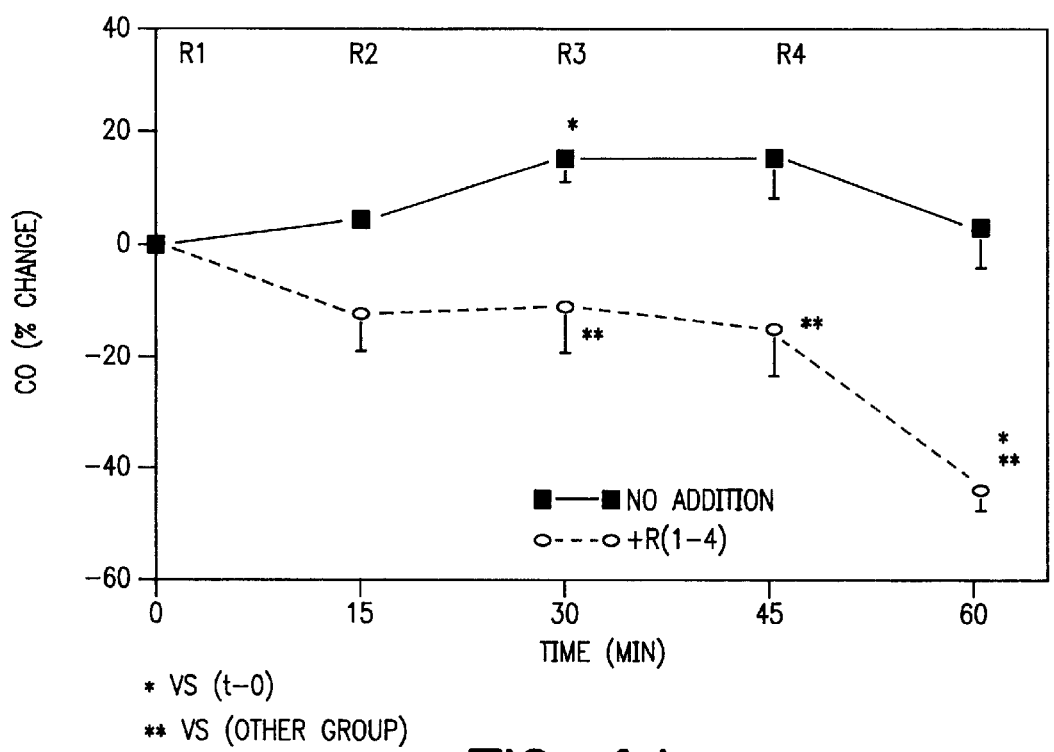
FIG. 4d illustrates changes in cardiac output in isolated working rat heart following gradual addition of R-verapamil to recirculating perfusate.

Using the same methodology, the data obtained showing percent change in cardiac output using varying amounts of R-verapamil, were plotted as a percent of baseline values determined during the pre-drug stabilization period, and are graphically represented in FIG. 4d.

TABLE 4

Summary

| Indices | HR | PSP | RPP | CO |
|---|---|---|---|---|
| N.A. | *(+30') | *(+45,60') | n.s. | *(+30') |
| R1 (50 ng/ml) | n.s. | n.s. | n.s. | n.s. |
| R2 (200 ng/ml) | n.s. | n.s. | n.s. | n.s. |
| R3 (450 ng/ml) | n.s. | n.s. | n.s. | n.s. |
| R4 (950 ng/ml) | * | n.s. | * | * |

*significantly different from baseline values

With respect to R-verapamil, it appears that this enantiomer has little effect on cardiac function until levels reach 950 ng/ml (FIG. 4c). This suggests that S is the much more potent of the verapamil enantiomers. Also, it is apparent, that R has virtually no effect on $Ca^{2+}$ channels since PSP (FIG. 4b) remains unaffected by increasing levels of R. The reduction in cardiac output (FIG. 4d) is likely due to the effect of R on heart rate (FIG. 4a) suggesting a direct negative chronotropic effect of this enantiomer. The slight changes in heart rate, peak systolic pressure and cardiac output that appear in hearts perfused without verapamil may be due to ongoing changes in $Ca^{2+}$ homeostasis.

In the following example, the effects of different ratios of R- and S-verapamil on electrophysiological properties of the canine heart along with peripheral circulation in the conscious animal were compared.

EXAMPLE 5
PREPARATION OF ANIMALS

Figure 5:
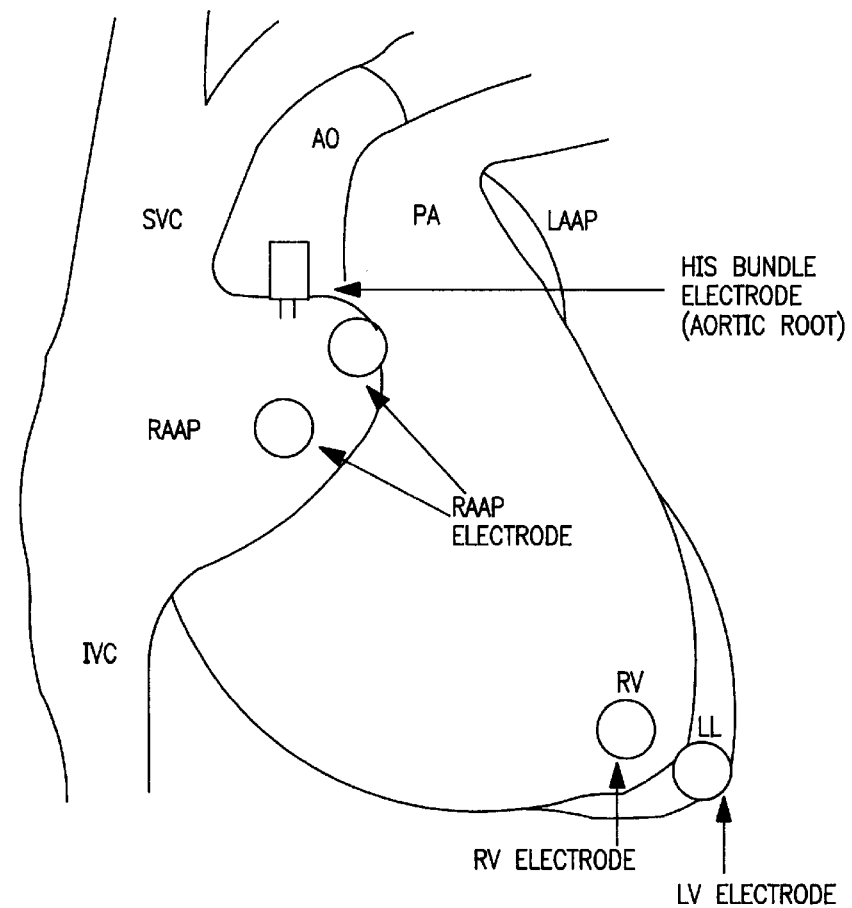
FIG. 5 shows placement of electrodes in the canine heart.

Fourteen adult mongrel dogs of either sex weighing between 19 and 25 kg were prepared for chronic electrophysiologic investigation by implanting epicardial electrodes and an indwelling aortic catheter. The dogs were fasted overnight and initially anesthetized with halothane on the day of surgery. After tracheal intubation, anesthesia was maintained with isoflurane and oxygen via positive pressure ventilation to keep end tidal carbon dioxide within the normal range. Muscular relaxation was induced by pancuronium. A right thoracotomy was performed in the fifth intercostal space. Three bipolar electrode pairs were sutured to the epicardial surface of the right atrial appendage and on the right and left ventricular apex (FIG. 5). A bipolar electrode was sutured to the right atrium close to the anatomical region of the sinoatrial node. A bipolar plunge electrode was placed into base of the interventricular septum to record a His bundle electrogram. An indwelling arterial catheter was placed into the aorta through the left femoral artery after surgical exposure of the artery at the inner side of the hind limb. All electrode leads were subcutaneously tunneled and exited through the skin between the scapulae. Incisions were closed in anatomic fashion and standard postoperative methods of analgesia were provided with 0.015 mg/kg of buprenorphine (Buprenex®, Reckitt & Colman, Hull, UK) and two times of 25 mg/kg cefazolin (Cefazolin Sodium®, SoloPak Laboratories, Elk Groove Village, Ill.) and dogs were allowed to recover from surgery for a period of seven days prior to testing.

Electrical signals from the bipolar electrodes, after suitable amplification in a custom built preamplifier (gain 1000), were filtered in a separate custom designed and built common mode rejection amplifier with a bandpass filter of 10–1000 Hz and individually adjusted for signal strength (maximal gain 400). From here the signals were sent to a desktop computer (Apple Macintosh Centris 650®, Capertino, Calif.), digitally converted with MacADIOS ll A-D board (GW Instruments®, Somerville, Mass.), displayed and stored for the subsequent analyses with SuperScope II (GW Instruments®, Somerville, Mass.). The surface ECG was amplified (78213C, Hewlett-Packard®, Fort Collins, Colo.), displayed, and the heart rate (HR) continuously measured (peak detector), using a separate monitor (model HP 78303A, Hewlett-Packard®, Fort Collins, Colo.). Right atrial appendage (RA), right ventricular apex (RVA) and His bundle electrograms (HB) were recorded, simultaneously. Cardiac pacing was performed with a programmed cardiac stimulator (model SEC3 102, Nihon Kohden®, Tokyo, Japan). All measurements of conduction times were made during spontaneous sinus rhythm.

The His bundle electrode (HBE) was advanced into the base of the interatrial septum from the aortic root. The electrode was advanced from a point located just behind and to the right of the origin of the right coronary artery. The HBE was slowly advanced parallel to the aorta, inferiorly and slightly anteriorly until a well discernible His potential was recorded. AV conduction (AH) interval was measured as the time difference (ms) between the onset of the initial rapid deflection in the RA electrogram to the beginning of the His potential in the HB electrogram. His-ventricular (HV) conduction time interval (ms) was measured from the beginning of the His potential (HBE) to the initial deflection of the QRS complex wave (earliest left ventricular activation) in a simultaneously recorded surface ECG lead II.

As an indicator of automaticity, sinus node recovery time (SNRT) was determined by pacing the right atrial appendage (30 s at 180 and 200 beats/min at 2 msec pulse duration; 2×threshold). SNRT was measured from the last pacing spike to the first spontaneous atrial activity on the His bundle electrogram after cessation of pacing (ms).

To determine the effective refractory period of the ventricular myocardium (ERPv), the ventricular excitation threshold was first determined by finding the minimum voltage required to produce a conducted ventricular complex with an extrastimulus duration of 2 msec delivered 300 ms after the R- wave of the lead II ECG. Using a twice threshold stimulus, the ventricle was paced at 171, or 200, beats/min, depending on intrinsic rhythm. A timed extrastimulus (S2) was delivered 300 ms after the preceding pacing spike (S1). The S1–S2 coupling was decreased incrementally until the ventricle failed to produce a conducted response. The effective refractory period was defined as the longest S1–S2 interval which failed to produce a ventricular response.

Systolic (SBP) and diastolic blood pressures (DBP) were measured using a pressure transducer (Baxter Uniflow, Baxter®, Deerfield, Ill.) and an amplifier (model HP 78205 D, Hewlett-Packard®, Fort Collins, Colo.), and they were subsequently digitized and recorded for determination of mean arterial pressure (MAP).

Verapamil was dissolved in 5% dextrose and water (2.0 g/ml). A bolus dose was administered over 2 min with an infusion pump (model 5006100, Harvard @, South Natick, Mass.).

During the postoperative period, each dog was trained to stand quietly in a sling during electrophysiological monitoring. Prior to measurement, electrical signals in each dog were monitored to verify the absence of spontaneous arrhythmias other-than normal respiratory sinus arrhythmias.

From the resting dog, 5 channel records were obtained at a sampling rate of 1 kHz per channel for 7 min to determine the following conduction intervals: AH, HV, QRS, QT and HR. A corrected QT interval [$QTc=QT$ interval in ms/ $(R-R$ interval in $s)^{1/2}$] was also calculated. In addition, systolic (SBP) and diastolic blood pressure (DBP) were recorded, followed by ERPv determination. Next, the heart was paced from the sinoatrial electrode pair to determine SNRT. Cumulative dose-response relations of verapamil (0.1, 0.2 and 0.4 mg/kg) in different R/S ratios (100/0, 90/10, 80/20, 50/50 and 20/80) were established. On five different days, different R/S ratios of verapamil were randomly selected for study. On each study day, the dog was fasted overnight, transported to the laboratory and measurements were taken prior to and after each incremental dose of intravenous verapamil. Fifteen minutes were allowed between doses.

Statistical Analysis

Data were processed and statistically analyzed, using an Apple Macintosh desktop computer and standard statistics software package. Two-way ANOVA with repeated measures were performed within each ratio, followed by the Fisher's protected least significant difference test (Fisher's PLSD) or the Scheffe test to determine the significance of differences between doses. Comparison between each ratio was determined using ANOVA followed by Newman-Keuls test. A chi square test of statistical independence was performed on data for AV block. Multiple linear regression analysis was used to compare the interactions between hemodynamic and conduction variables. All data were expressed as mean values SEM, and differences were considered to be significant when $P<0.05$.

Results

Fourteen dogs were used in this study, 4 dogs were excluded from data analysis because three dogs died before measurement and 1 dog developed ventricular escape beats after surgery in the absence of intervention.

Figure 6A:
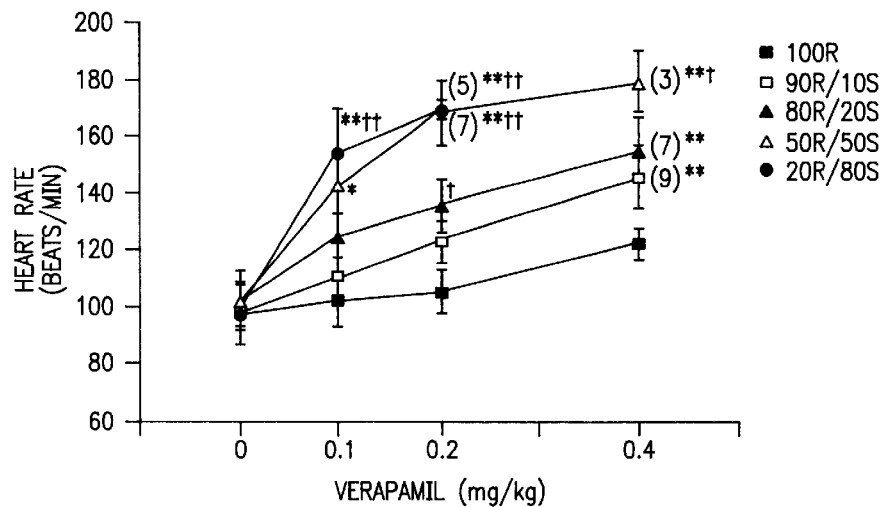
FIGS. 6a, 6b and 6c show the peak effects of all concentrations and all dosages of R- and S- verapamil on heart rate (6a), mean arterial pressure (6b) and AH time (6c) in the canine heart.

Baseline heart rate (HR) was the same prior to administration of each mixture of verapamil. Initially, after each infusion of verapamil, an initial increase in HR occurred. The increase in HR was similar in fashion between each mixture (table 5), and the degree of increase was dose-dependent. Increase in HR during the 20R/80S-verapamil mixture was 9 times greater than that observed following 100R-verapamil. FIG. 6 a shows these results in graph form.

TABLE 5

| | | Changes in heart rate (beats per min) | | | | | |
|---|---|---|---|---|---|---|---|
| | N | 0 min | 1 min | 2 min | 3 min | 4 min | 5 min |
| control | | | | | | | |
| 100/0S | 10 | 98 ± 10 | | | | | |
| 90/10S | 10 | 99 ± 5 | | | | | |
| 80/20S | 10 | 103 ± 9 | | | | | |
| 50/50S | 10 | 103 ± 6 | | | | | |
| 20/80S | 10 | 98 ± 6 | | | | | |
| 0.1 mg/kg | | | | | | | |
| 100/0S | 10 | 103 ± 9 | 95 ± 7 | 98 ± 8 | 93 ± 7 | 91 ± 8 | 92 ± 8 |
| 90/10S | 10 | 111 ± 7 | 103 ± 7 | 104 ± 6 | 101 ± 8 | 101 ± 7 | 103 ± 7 |
| 80/20S | 10 | 125 ± 8 | 126 ± 7† | 119 ± 7 | 115 ± 7 | 116 ± 8 | 123 ± 7† |
| 50/50S | 10 | 143 ± 11†§ | 135 ± 6††§ | 122 ± 7 | 118 ± 6* | 119 ± 7* | 125 ± 8† |
| 20/80S | 9 | 155 ± 13††§§ | 143 ± 11††§§ | 127 ± 10 | 124 ± 9*† | 113 ± 11** | 111 ± 8** |
| 0.2 mg/kg | | | | | | | |
| 100/0S | 10 | 106 ± 7 | 104 ± 8 | 99 ± 9 | 102 ± 9 | 96 ± 8 | 95 ± 9 |
| 90/10S | 10 | 123 ± 7§ | 124 ± 10§ | 116 ± 7 | 113 ± 6 | 116 ± 7 | 118 ± 8 |
| 80/20S | 10 | 136 ± 9†§ | 134 ± 8†§ | 129 ± 7†§ | 124 ± 7 | 125 ± 8 | 123 ± 9 |
| 50/50S | 7 | 169 ± 4††§§ | 164 ± 8†§§ | 149 ± 10††§§ | 149 ± 10††§§ | 147 ± 12††§§ | 147 ± 13††§ |
| 20/80S | 5 | 168 ± 10††§§ | 166 ± 9††§§ | 154 ± 8†§§ | 141 ± 11†§ | 155 ± 16††§ | 146 ± 4††§§ |
| 0.4 mg/kg | | | | | | | |
| 100/0S | 10 | 123 ± 5 | 108 ± 6 | 109 ± 5 | 106 ± 7 | 108 ± 7 | 111 ± 6 |
| 90/10S | 9 | 145 ± 10§§ | 134 ± 9§§ | 128 ± 10§§ | 128 ± 11§ | 129 ± 10§§ | 125 ± 9§ |
| 80/20S | 7 | 155 ± 12§§ | 153 ± 11††§§ | 149 ± 10††§§ | 147 ± 10††§ | 140 ± 7†§ | 135 ± 9 |
| 50/50S | 3 | 180 ± 11†§§ | 171 ± 7††§§ | 162 ± 3††§§ | 163 ± 5†§§ | 162 ± 4††§§ | 161 ± 9†§ |
| 20/80S | 0 | | | | | | |

Values are expressed as mean ± SE.
*$P < 0.05$, **$P < 0.01$, compared with 0 min in the same dosage.
†$P < 0.05$, ††$P < 0.01$, compared with 100/0S in the same dosage.
§$P < 0.05$, §§$P < 0.01$, compared with control in the same ratio.

The occurrence of second and third degree AV conduction block was observed in all animals receiving the 20R/80S-verapamil mixture, 7 animals in 50R/50S-verapamil, and 3 animals in 80R/20S-verapamil at the dosage of 0.4 mg/kg. At the dosage of 0.2 mg/kg, 5 animals in 20R/80S-verapamil and 3 animals in 50R/50S-verapamil had AV conduction block. Data from those animals in which AV conduction block appeared were excluded from data analysis.

Figure 6B:
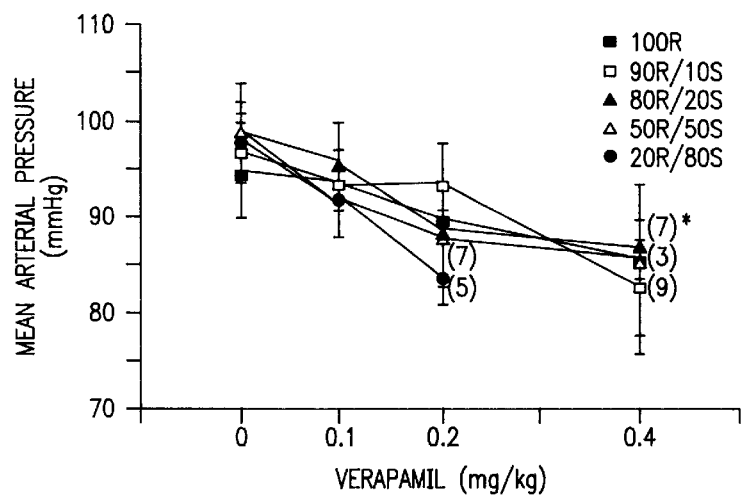

Baseline mean arterial pressure (MAP) was 95–99 mm Hg, and there was no significant difference between baseline values prior to each mixture of verapamil (table 6). Initially, after injection of verapamil, MAP was reduced. The decline in MAP occurred in a dose-dependent manner with 20R/80S-verapamil producing 3 times greater decrease than the 100R-verapamil. Recovery of the decrease MAP was slower in 20R/80S-verapamil compared with any other groups. FIG. 6b shows these results in graph form.

TABLE 6

| | | Changes in mean arterial pressure (mmHg) | | | | | |
|---|---|---|---|---|---|---|---|
| | N | 0 min | 1 min | 2 min | 3 min | 4 min | 5 min |
| control | | | | | | | |
| 100/0S | 10 | 95 ± 4 | | | | | |
| 90/10S | 10 | 97 ± 3 | | | | | |
| 80/20S | 10 | 99 ± 2 | | | | | |
| 50/50S | 10 | 99 ± 5 | | | | | |
| 20/80S | 10 | 98 ± 4 | | | | | |
| 0.1 mg/kg | | | | | | | |
| 100/0S | 10 | 94 ± 3 | 95 ± 3 | 95 ± 2 | 95 ± 3 | 95 ± 3 | 95 ± 3 |
| 90/10S | 10 | 94 ± 3 | 97 ± 4 | 99 ± 3 | 99 ± 3 | 100 ± 4 | 99 ± 3 |
| 80/20S | 10 | 96 ± 3 | 99 ± 3 | 98 ± 3 | 99 ± 3 | 100 ± 3 | 100 ± 3 |
| 50/50S | 10 | 92 ± 4 | 97 ± 4 | 101 ± 5 | 102 ± 5 | 100 ± 4 | 104 ± 4 |
| 20/80S | 9 | 92 ± 4 | 97 ± 3 | 100 ± 3 | 100 ± 4 | 99 ± 4 | 101 ± 4 |
| 0.2 mg/kg | | | | | | | |
| 100/0S | 10 | 90 ± 3 | 97 ± 3 | 97 ± 3 | 94 ± 2 | 96 ± 2 | 92 ± 2 |
| 90/10S | 10 | 94 ± 4 | 98 ± 4 | 99 ± 4 | 99 ± 4 | 100 ± 4 | 101 ± 3 |
| 80/20S | 10 | 89 ± 2§ | 95 ± 4 | 94 ± 4 | 97 ± 4 | 99 ± 3 | 98 ± 3 |

TABLE 6-continued

Changes in mean arterial pressure (mmHg)

| | N | 0 min | 1 min | 2 min | 3 min | 4 min | 5 min |
|---|---|---|---|---|---|---|---|
| 50/50S | 7 | 88 ± 5 | 90 ± 3 | 101 ± 4 | 101 ± 6 | 101 ± 4 | 100 ± 5 |
| 20/80S | 5 | 84 ± 3 | 87 ± 4 | 93 ± 5 | 94 ± 5 | 97 ± 5* | 98 ± 3* |
| 0.4 mg/kg | | | | | | | |
| 100/0S | 10 | 86 ± 2 | 94 ± 2 | 98 ± 3** | 97 ± 3** | 99 ± 3** | 98 ± 3** |
| 90/10S | 9 | 83 ± 7 | 89 ± 7 | 90 ± 7 | 90 ± 7 | 93 ± 7 | 92 ± 7 |
| 80/20S | 7 | 87 ± 3§ | 95 ± 3 | 97 ± 3* | 101 ± 3** | 103 ± 3** | 103 ± 3** |
| 50/50S | 3 | 86 ± 8 | 87 ± 8 | 92 ± 7 | 97 ± 6 | 95 ± 8 | 98 ± 6 |
| 20/80S | 0 | | | | | | |

Values are expressed as mean ± SE.
*P < 0.05, **P < 0.01; compared with 0 min in the same dosage.
§P < 0.05, compared with control in the same ratio.

Figure 6C:
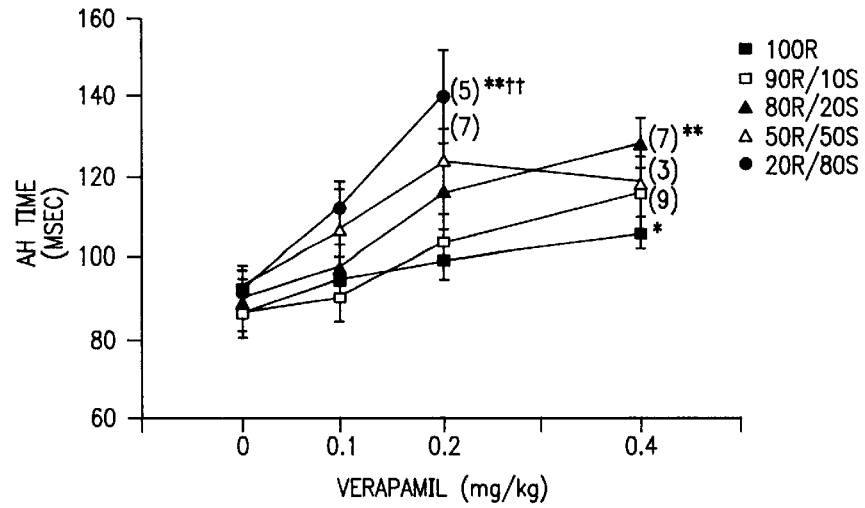

Baseline atrio-ventricular conduction (AH) times were not significantly different between each group of animals (table 7). The increase in AH time began 2 min after injection, and the degree of increase was larger in the higher S ratio drugs. The peak increase of AH time occurred during the 3 to 5 min period after the end of verapamil injection. Increases in AH time were dose-dependent with the 20R/80S-verapamil producing a 4 times greater effect than the 100R-verapamil. FIG. 6c shows these results in graph form.

Baseline HV times and QRS intervals in each group were 27.9–29.5 ms and 56–59, respectively. The different mixtures of S- and R-verapamil had no effect on these parameters.

TABLE 7

Changes in AH time (msec)

| | N | 0 min | 1 min | 2 min | 3 min | 4 min | 5 min |
|---|---|---|---|---|---|---|---|
| control | | | | | | | |
| 100/0S | 10 | 87 ± 6 | | | | | |
| 90/10S | 10 | 87 ± 5 | | | | | |
| 80/20S | 10 | 90 ± 5 | | | | | |
| 50/50S | 10 | 93 ± 5 | | | | | |
| 20/80S | 10 | 92 ± 5 | | | | | |
| 0.1 mg/kg | | | | | | | |
| 100/0S | 10 | 88 ± 5 | 94 ± 4 | 93 ± 5 | 93 ± 5 | 95 ± 5 | 95 ± 5 |
| 90/10S | 10 | 87 ± 6 | 88 ± 6 | 90 ± 6 | 91 ± 6 | 89 ± 6 | 89 ± 7 |
| 80/20S | 10 | 90 ± 4 | 95 ± 5 | 97 ± 5 | 98 ± 5 | 96 ± 5 | 96 ± 6 |
| 50/50S | 10 | 97 ± 16 | 107 ± 12 | 105 ± 9 | 106 ± 8 | 104 ± 7 | 104 ± 6 |
| 20/80S | 9 | 88 ± 5 | 100 ± 5 | 106 ± 5* | 107 ± 5* | 111 ± 6** | 112 ± 5** |
| 0.2 mg/kg | | | | | | | |
| 100/0S | 10 | 93 ± 4 | 99 ± 5 | 97 ± 5 | 98 ± 4† | 98 ± 4 | 99 ± 5 |
| 90/10S | 10 | 91 ± 7 | 95 ± 8 | 99 ± 8 | 98 ± 7†† | 97 ± 7 | 104 ± 7 |
| 80/20S | 10 | 99 ± 5 | 111 ± 8 | 115 ± 9§ | 113 ± 8 | 115 ± 9§ | 116 ± 9§ |
| 50/50S | 7 | 96 ± 8 | 117 ± 11 | 112 ± 7 | 118 ± 9 | 117 ± 8 | 124 ± 8*§ |
| 20/80S | 5 | 110 ± 10 | 126 ± 11§ | 133 ± 10§§ | 140 ± 12§§ | 127 ± 14§§ | 130 ± 11§§ |
| 0.4 mg/kg | | | | | | | |
| 100/0S | 10 | 97 ± 4 | 106 ± 5 | 106 ± 4 | 104 ± 4 | 104 ± 5 | 105 ± 5 |
| 90/10S | 9 | 100 ± 9 | 111 ± 10 | 116 ± 10 | 116 ± 12 | 114 ± 9 | 112 ± 10 |
| 80/20S | 7 | 111 ± 5 | 121 ± 4§ | 123 ± 5§ | 125 ± 6§ | 127 ± 6*§ | 129 ± 6*§ |
| 50/50S | 3 | 101 ± 10 | 112 ± 10 | 116 ± 5 | 117 ± 7 | 119 ± 8 | 113 ± 5 |
| 20/80S | 0 | | | | | | |

Values are expressed as mean ± SE.
*P < 0.05, **P < 0.01, compared with 0 min in the same dosage.
†P < 0.05, ††P < 0.01, compared with 20/80S in the same dosage.
§P < 0.05, §§P < 0.01, compared with control in the same ratio.

The effect of verapamil on the QTc interval is shown in table 8. After 0.1 and 0.2 mg/kg doses of the 20R/50S-verapamil and 50R/50S-verapamil mixtures, QTc interval was significantly increased compared with 100R-verapamil. However, QTc interval in each mixture did not change significantly compared with its baseline, no-drug value.

Figure 7:
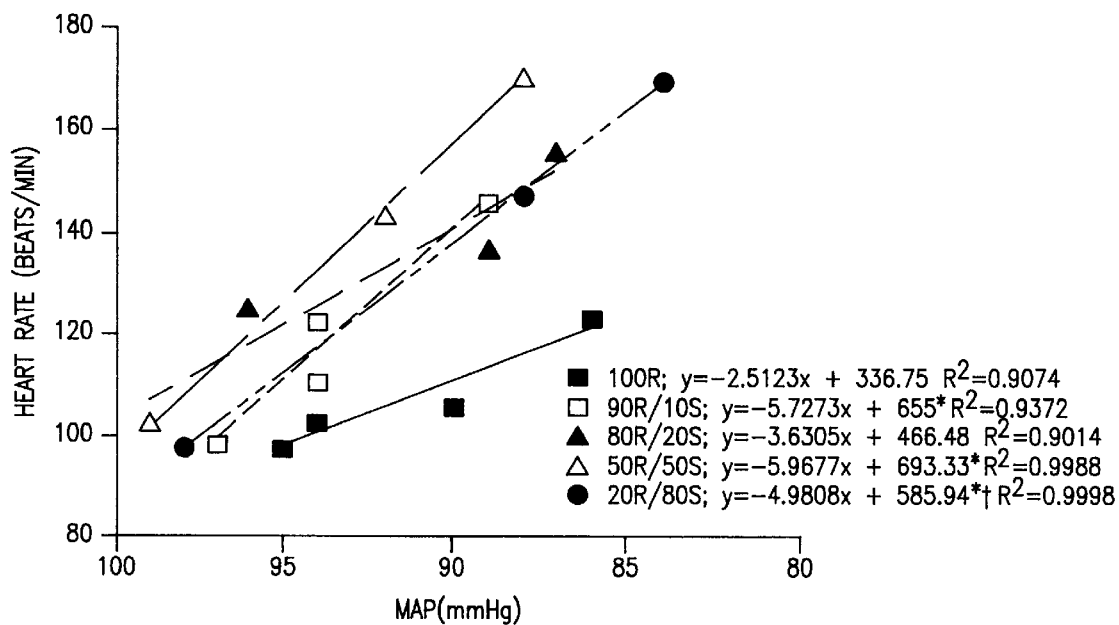
FIG. 7 graphically shows the mean arterial pressure, heart rate for varying R/S verapamil concentrations in the canine heart.

Multiple linear regression analyses demonstrated that the interaction between MAP and HR with 100R-verapamil was associated with the least increase in heart rate measured against a drop in blood pressure (FIG. 7). Ratios of 50R/50S-verapamil and 20R/80S-verapamil produced the greatest rate of increase in HR as opposed to a drop in MAP. In

TABLE 8

Changes in QTc interval (msec)

|  | N | 0 min | 1 min | 2 min | 3 min | 4 min | 5 min |
|---|---|---|---|---|---|---|---|
| control |  |  |  |  |  |  |  |
| 100/0S | 10 | 263 ± 10 |  |  |  |  |  |
| 90/10S | 10 | 275 ± 6 |  |  |  |  |  |
| 80/20S | 10 | 269 ± 10 |  |  |  |  |  |
| 50/50S | 10 | 278 ± 6 |  |  |  |  |  |
| 20/80S | 10 | 270 ± 8 |  |  |  |  |  |
| 0.1 mg/kg |  |  |  |  |  |  |  |
| 100/0S | 10 | 264 ± 7 | 261 ± 7 | 265 ± 8 | 260 ± 6 | 258 ± 7 | 259 ± 6 |
| 90/10S | 10 | 281 ± 5 | 273 ± 8 | 274 ± 6 | 269 ± 8 | 271 ± 7 | 274 ± 6 |
| 80/20S | 10 | 274 ± 8 | 280 ± 5 | 279 ± 5 | 273 ± 6 | 275 ± 7 | 285 ± 4† |
| 50/50S | 10 | 302 ± 12† | 295 ± 6† | 287 ± 8 | 284 ± 7 | 286 ± 8 | 291 ± 8† |
| 20/80S | 9 | 304 ± 9†§ | 293 ± 8† | 287 ± 9 | 285 ± 8 | 276 ± 11* | 277 ± 8* |
| 0.2 mg/kg |  |  |  |  |  |  |  |
| 100/0S | 10 | 270 ± 4 | 268 ± 5 | 266 ± 7 | 267 ± 8 | 260 ± 6 | 263 ± 8 |
| 90/10S | 10 | 279 ± 6 | 283 ± 5 | 282 ± 5 | 278 ± 7 | 278 ± 6 | 284 ± 5 |
| 80/20S | 10 | 286 ± 5 | 286 ± 6 | 281 ± 5 | 274 ± 5 | 278 ± 6 | 278 ± 7 |
| 50/50S | 7 | 302 ± 7†† | 304 ± 10†† | 295 ± 11 | 292 ± 9 | 293 ± 8† | 295 ± 9† |
| 20/80S | 5 | 303 ± 8†† | 301 ± 8† | 288 ± 11 | 278 ± 10 | 289 ± 10† | 293 ± 12 |
| 0.4 mg/kg |  |  |  |  |  |  |  |
| 100/0S | 10 | 285 ± 6 | 269 ± 5 | 271 ± 5 | 271 ± 5 | 277 ± 6 | 275 ± 7 |
| 90/10S | 9 | 282 ± 7 | 280 ± 4 | 276 ± 6 | 276 ± 7 | 279 ± 7 | 275 ± 7 |
| 80/20S | 7 | 291 ± 7 | 289 ± 7 | 286 ± 8 | 284 ± 6 | 282 ± 5 | 281 ± 5 |
| 50/50S | 3 | 308 ± 11 | 301 ± 18† | 291 ± 19 | 283 ± 23 | 295 ± 21 | 294 ± 20 |
| 20/80S | 0 |  |  |  |  |  |  |

Values are expressed as mean ± SE.
QTc = (QT interval in msec)/(R-R interval in Sec)
*P < 0.05, compared with 0 min in the same dosage.
†P < 0.05, ††P < 0.01, compared with 100/0S in the same dosage.
P < 0.05, compared with control in the same ratio.

Baseline ERPv ranged between 130–137 ms in all groups. With higher S-ratio verapamil the ERPv was shortened but the changes were not statistically significant.

The control values of SNRT at 180 and 200 beats/min were same in each verapamil mixture. SNRT was shortened by each ratio of verapamil paced at 180 beats/min and 200 beats/min in a dose dependent manner, and shortening was greater in higher S-isomer mixtures. There was only a significant decrease in 90R/10S-verapamil and 50R/50S-verapamil paced at 200 beats/min.

Peak Effect Comparison of Hemodynamics and the Conduction System Between Each Ratio Group There was a different time course in the onset of the effect on the hemodynamics versus conduction system effects (table 5–7). To clarify the effect of different mixtures of verapamil on each parameter, the effect of each mixture using its peak effect and absolute value of the response were compared.

FIG. 7 shows the peak effects of all concentrations and all dosages on hemodynamic variables and A-H conduction time. The effect of verapamil on MAP showed no significant difference between mixtures. The higher S-verapamil affected HR to a greater extent at a lower dosage. There was a drastic increase in HR following administration of the 20R/80S-verapamil and 50R/50S-verapamil mixtures compared with that after 100R-verapamil. Higher S-verapamil was more potent in lengthening the AH time.

the relation between AH time related to MAP and HR, multiple regression analysis failed to show any significant differences in the slope factor between ratios.

The results indicate that all R/S mixtures of verapamil produced hypotension and baroreceptor mediated tachycardia, followed by the lengthening of AH conduction time. A higher R-verapamil produced a smaller increase in the heart rate for a given drop in mean arterial pressure, while higher S-verapamil produced greater increase of HR and prolongation of AH time for a given drop in blood pressure and a greater number of incidents of AV blocks. The restoration from those changes was delayed in higher S-mixture compared with that in higher R-verapamil.

In the present study, using a conscious dog model, there was a greater change in HR with a higher S-isomer verapamil. It has been reported that the direct inhibitory action of verapamil on sinus node automaticity is masked by baroreflex tachycardia and that anesthesia masks this response. Therefore, we used dogs in the conscious, unsedated state, which is thought as a better model to study a drug effects on electrical activity, ventricular function, baroreceptor activation, and systemic effects. Increase of HR shown in all R/S mixture verapamil just after infusion is due to activation of baroreceptor reflex secondary to peripheral vasodilation. These changes in HR were shown in previous reports using racemic verapamil in conscious state studies.

Class III antiarrhythmic drugs increase QTc and ERPv. During the higher S-verapamil infusion, an increase of QTc interval was observed, but ERPv did not change. Verapamil has been reported to block the potassium current in different the medical indications, i.e. control of conduction abnormalities or lowering of blood pressure. Pharmaceutical compositions containing the R:S ratios shown below are one aspect of the present invention.

TABLE 9

| Route/Dosage Form | Amount | Range of ratios (R:S) | Indication |
|---|---|---|---|
| Intravenous | 2 mg–25 mg in adults | 1:99 to 45:55 | Control of conduction abnormalities such as supraventricular tachycardia |
| Oral-Immediate Release | 15 mg–150 mg min adults (administered 2–4 times per day) | 1:99 to 45:55, preferably 1:99 to 35:65 | Same |
| Oral-Sustained Release | 30 mg to 300 mg in adults (administered once per day) | 1:99 to 45:55 preferably 1:99 to 25:75 | Same |
| Transdermal | 10–100 mg | 1:99 to 45:55 | Same |
| Intravenous | 4 mg–50 mg in adults | 99:1 to 55:45 | Lowering of blood pressure optimized for impact on heart rate or cardiac muscle contractility |
| Oral-Immediate Release | 60 mg–600 mg in adults (administered 2–4 times per day) | 99:1 to 55;45 preferably 99:1 to 65:35 | Same |
| Oral-Sustained Release | 120 mg to 2400 mg in adults (administered once per day) | 1:99 to 45:55, preferably 99:1 to 75:25 | Same |
| Transdermal | 10–100 mg | 99:1 to 45:55 | Same | cells using the voltage-clamp methodology. Repolarizadon of ventricular myocardium is dependent mainly on various potassium currents. Therefore, it is reasonable to hypothesize that the blockade of potassium currents caused by verapamil is responsible for the longer depolarization phase of the action potential leading to an increase in QTc interval.

Higher S-verapamil has potential effects on hemodynamics and AV conduction system. The peripheral and cardiac electrophysiologic properties of various nonracemic verapamil mixtures are mainly attributable to the level of S-isomer. The higher R-verapamil had smaller effect of reflex tachycardia and AV conduction block while preserving MAP compared with those of higher S-mixture. Therefore, the nonracemic verapamil mixtures can produce different magnitude of effects on the peripheral hemodynamics and AV conduction system, that is attributed to the relative ratio of R- and S-isomer.

Based on the studies outlined above, it is apparent that combining the enantiomers of verapamil in differing amounts yields different pharmacological effects. Thus, one can target treatment of a condition by appropriate selection of the R/S ratio of verapamil administered to a patient.

As noted earlier, and as recognized in the literature, the body metabolizes racemic verapamil differently depending on the dosage form used. Further, R- and S-verapamil are metabolized at different rates in the body.

Accordingly, it is an aspect of this invention to provide a pharmaceutical composition and a process for preparing a pharmaceutical composition where R-verapamil and S-verapamil are both present, but in unequal amounts. Depending on the intended use, the composition may contain either a greater quantity of R-verapamil or a greater quantity of S-verapamil.

The following Table 9, shows the suitable dosage amount and range of ratios of R-verapamil to S-verapamil (R:S ratios), for each of four dosage routes or forms in relation to It is also a goal of the present invention to provide drug formulations having amounts of R and S verapamil which will yield a targeted R:S ratio in plasma. The relative amounts of R- and S-verapamil needed to achieve a targeted ratio in plasma will vary for each dosage form since the dosage form affects how verapamil is metabolized.

Verapamil is currently commercially available in three dosage forms: intravenous, oral immediate release and oral sustained release. Each of these forms will require different amounts of the R and S enantiomers to achieve a targeted plasma R:S ratio.

The results obtained in example 1 suggest that an R:S ratio of approximately 80:20 will have a decreased tissue-to-plasma partition coefficient compared to the single enantiomer or the racemate. This is expected to translate into a larger fraction of the verapamil remaining in the circulatory plasma where it has access to receptors in the peripheral vasculature, rather than portioning into tissues. This provides a more favorable antihypertensive profile. Based on the relative potencies of the R- and S-verapamil for cardiac conduction activities, a R:S ratio greater than 80:20 is preferred. Accordingly, a R:S ratio in the plasma of 85:15 is believed desirable to achieve an antihypertensive effect, while minimizing side effects. Targeted plasma R:S ratios in the range of 90/10 to 70/30 are also believed to achieve the antihypertensive effects while minimizing side effects.

Figure 8:
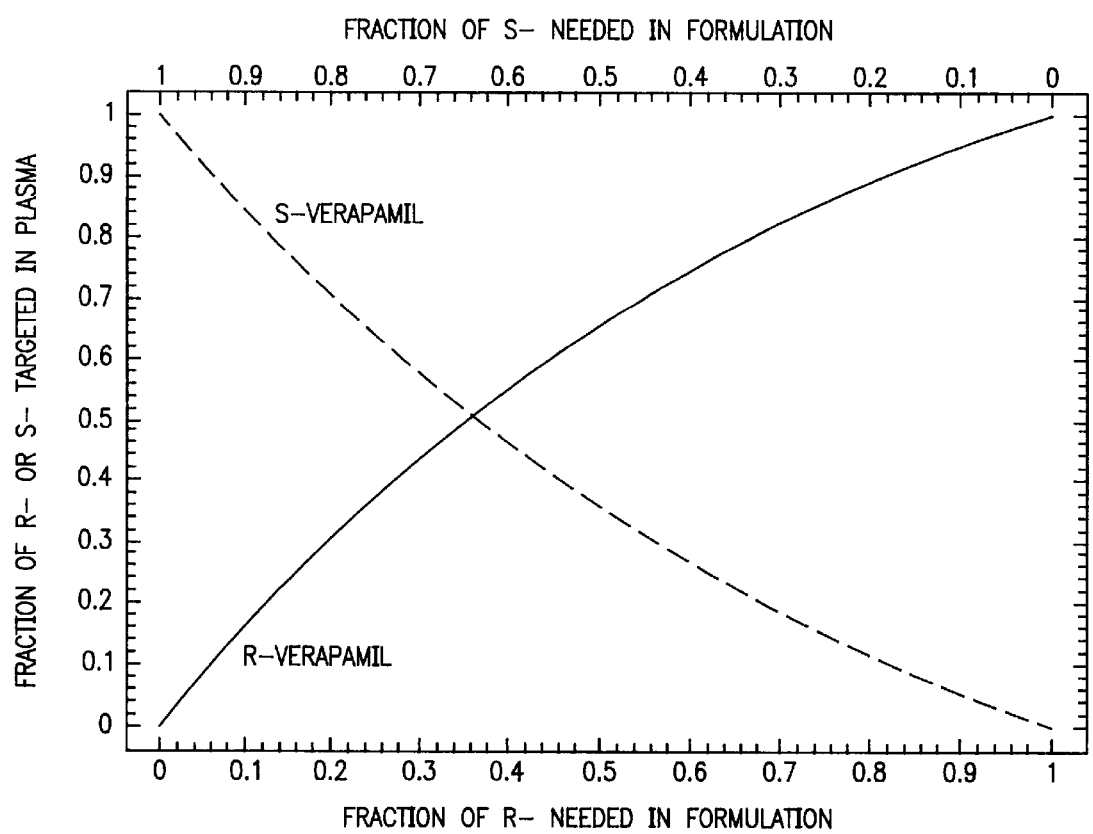
FIG. 8 is a graph used to simulate fractions of R- and S-verapamil in an intravenous formulation to achieve a targeted R- or S-verapamil fraction in plasma.
Figure 9:
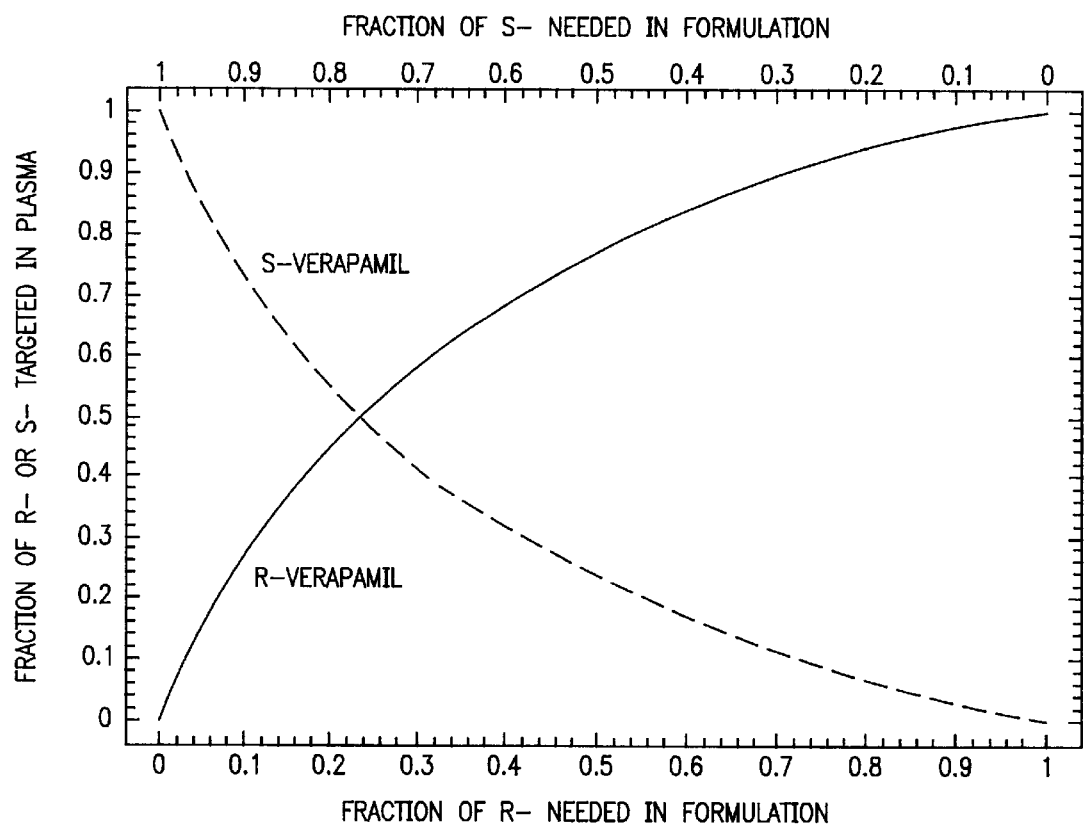
FIG. 9 is a graph used to simulate fractions of R- and S-verapamil in an immediate release oral formulation to achieve a targeted R- or S-verapamil fraction in plasma.
Figure 10:
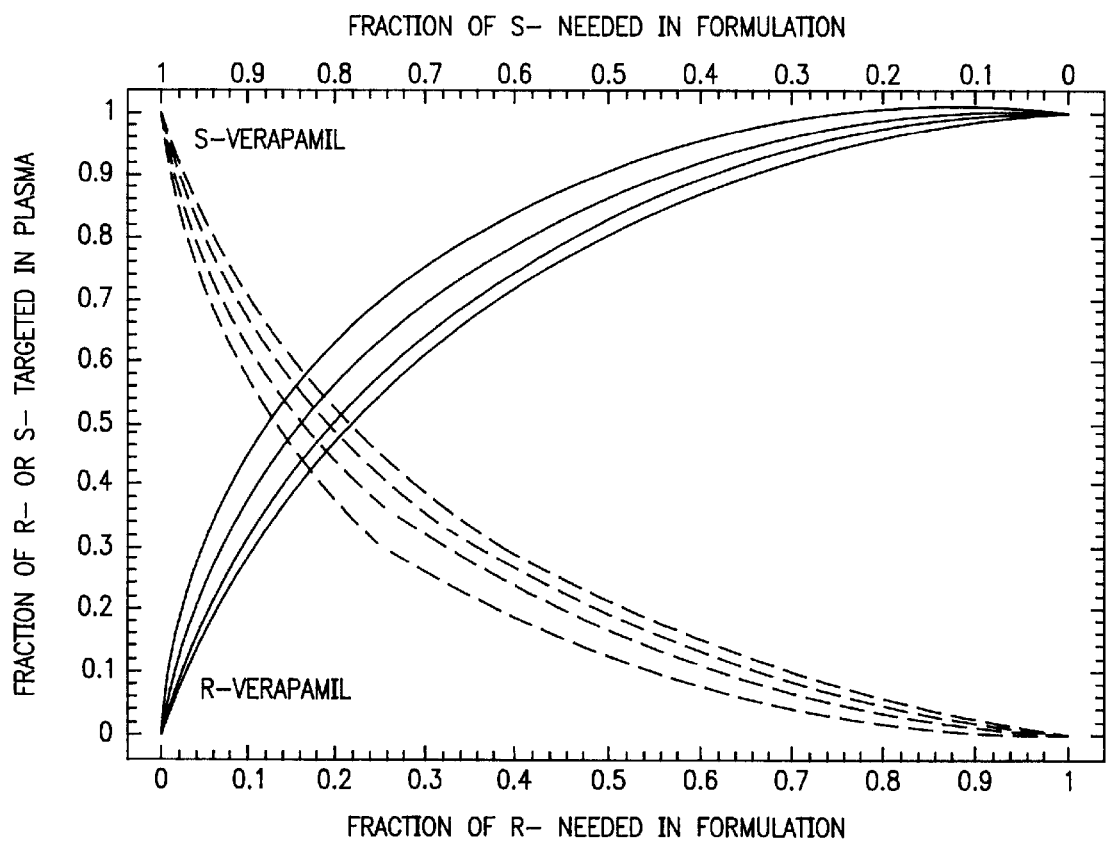
FIG. 10 is a graph used to simulate fractions of R- and S-verapamil in an oral sustained release formulation for a targeted R- or S-verapamil fraction in plasma.

Using the information contained in FIGS. 8–10, one can determine the relative amounts of the enantiomers for each of the three commercially available dosage forms required to achieve a 85:15 R:S ratio.

The information in FIGS. 8–10 is derived from data showing the mean R-verapamil:S-verapamil ratio observed following intravenous and oral dosing of racemic verapamil, as reported in Longstreth, "Verapamil A Chiral Challenge to the Pharmacokinetic and Pharmacodynamic Assessment of Bioavailability and Bioequivalence" in *Drug Stereochemistry*, Irving W. Wainer, Ed. (1993). The data reported in Table 10 is derived from similarly obtained data showing the mean R-verapamil:S-verapamil ratio observed following oral dosing of sustained release formulations containing varying quantities of verapamil.

For example, referring to FIG. 8, to achieve a target R:S ratio of 85:15, an IV solution with a R:S ratio of 75:25 should be used. If an oral immediate release formulation is desired, a tablet or oral solution with on enantiomeric ratio of 65:35 is needed, according to the information contained in FIG. 9. FIG. 10 shows information for sustained release formulations, at varying doses. For a low dose (e.g, 120 mg/day) an enantiomeric ratio of 35:65 can be used to achieve the target R:S ratio. When using a more typical dose of 240 mg/day, FIG. 10 shows a ratio of 55:45 R:S should be used to achieve the targeted plasma values. In FIG. 10, the left-most curve is for the lower doses and the right-most curve for the highest doses.

As a further example of designing drug formulations to obtain desired R:S plasma levels, and thereby achieve desirable pharmaceutical effects, is the case where verapamil is used to produce rapid and reliable control of supraventricular tachycardia. When administered intravenously, racemic verapamil has been found to work well for this purpose. Oral dosage forms have been less effective for this indication.

By referring to FIG. 8, and selecting 0.5 on the horizontal axis and reading upwards, it can be seen that the racemic intravenous formulation achieved plasma levels of 0.36 S-verapamil (dotted line) and 0.64 R-verapamil (solid line). Since this ratio produces good results, oral dosage forms which achieve this 64:36 R:S ratio in plasma would be desirable.

Using the 64:36 R:S target ratio and the information contained in FIGS. 9 and 10, one can determine that an R:S ratio of 35:65 is desired in the oral immediate release formulation. Using an intermediate dose, an R:S ratio of about 25:75 in the sustained release formulation is desired.

To treat angina, it is believed another target R:S plasma ratio may be appropriate. In treating angina, one may assume that reducing oxygen consumption by the heart muscle is important. Thus, one would want to get drug into the cardiac tissue where it will slow the beating rate of the heart and reduce its contractile force. S-verapamil is more effective at achieving these functions than R-verapamil. Further, according to the phase diagram in FIG. 1, the expectation is that the partitioning of drug into tissue will be greatest at approximately the 50:50 ratio.

Targeting a 50:50 ratio for plasma concentrations and utilizing the information contained in FIGS. 8–10, an IV formulation would have to have a 35:65 R:S ratio, an immediate release would have to have a 24:76 ratio and the sustained release formulation would have R:S ratio between 12:88 and 20:80, in accordance with the present invention.

Other plasma ratios, such as 60:40 may also be considered useful to treat angina.

Thus, in accordance with the present invention, one can manipulate drug dosage formulations by incorporating varying amounts of the R and S enantiomers of verapamil to achieve targeted plasma levels of the R and S enantiomers. The targeted plasma levels of the enantiomers are selected to achieve the desired treatment effects, while minimizing adverse side effects.

While certain targeted plasma levels are discussed herein, they are for exemplification, and the current invention is not to be considered limited to specific target plasma R:S ratios.

Moreover, while specific dosage forms are discussed herein, those being those now commercially available, including intravenous, oral immediate release and oral sustained release, it is to be understood that the invention is not limited to any specific dosage form or route of administration.

Indeed, the pharmaceutical compositions of the present invention may be specially formulated for oral administration in solid or liquid form, for parenteral injection, and/or for rectal or vaginal administration. They may be administered to humans and other animals for therapy for any suitable route of administration, including orally, nasally, as by, for example, a spray, rectally, intravaginally, parenterally, intracisternally and topically, as by powders, ointments or drops, including buccally and sublingually. The preferred routes of administration are orally and parenterally.

Regardless of the route of administration selected, pharmaceutical compositions of the present invention, are formulated into pharmaceutically-accepted dosage forms by conventional methods known to those of skill in the art.

The pharmaceutical compositions of the present invention comprise a mixture of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfite, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alphatocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be preferred by any methods well known in the art of pharmacy.

Methods for preparing these formulations or compositions include the step of bringing into association the mixture of the present invention with the carrier and, optionally, with one or more accessory ingredients. In general, the formulations are preferred by uniformly and intimately bringing into association the mixture of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the compound of the present invention as an active ingredient. The enantiomeric mixture of the present invention may also be administered as a bolus, electuary or paste.

In solid dosage forms of the invention for oral administration (capsules, tablets, pills, dragees, powders, granules and the like), the enantiomeric mixture is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as a dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacterial-retaining filter, or by incorporating sterilizing agents in the form of sterile solid compositions which can be dissolved in sterile water, or some other sterile, injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The enantiomeric mixture can also be in micro-encapsulated form, if appropriate, with one or more of the above-described excipients.

Liquid dosage forms for oral administration of the mixture of the invention include pharmaceutically-acceptable emulsions, microemulsions, solutions, suspensions, syrups and elixirs. In addition to the enantiomeric mixture, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the enantiomeric mixture, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of the mixture of this invention include powders, sprays, ointments, pastes, creams, lotions, gels, solutions, patches and inhalants. The enantiomeric mixture may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the mixture of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the mixture of the invention to the body. Such dosage forms can be made by dissolving, dispersing or otherwise incorporating the mixture of the present invention in a proper medium, such as an elastomeric matrix material. Absorption enhancers can also be used to increase the flux of the mixture across the skin. The rate of such flux can be controlled by either providing a rate-controlling membrane or dispersing the compound in a polymer matrix or gel.

Ophthalmic formulations, eye ointments, powders, solutions and the like, are also contemplated as being with the scope of this invention.

Pharmaceutical compositions of this invention suitable for parenteral administration comprise a mixture of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous and intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly (anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable media just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or nonaqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein. Specifically, the present invention is not limited to any specific dosage form or any specific R:S ratios, either in the plasma or in drug formulations.

What we claim is:

1. A pharmaceutical composition comprising a non-racemic mixture of R- and S-verapamil and a pharmaceutical excipient the relative amounts of R- and S-verapamil being chosen to achieve a predetermined target plasma level or a predetermined pharmaceutical activity.

2. A pharmaceutical composition according to claim 1, wherein the R-verapamil is present in a greater amount than the S-verapamil.

3. A pharmaceutical composition according to claim 1, wherein the S-verapamil is present in a greater amount than the R-verapamil.

4. A pharmaceutical composition according to claim 1, wherein the ratio of R-verapamil to S-verapamil (R:S) is 1:99 to 45:55.

5. A pharmaceutical composition according to claim 4, wherein the pharmaceutical excipient yields a composition which can be administered by a route selected from the group consisting of intravenous, oral and transdermal.

6. A pharmaceutical composition according to claim 1, wherein the ratio of R-verapamil to S-verapamil (R:S) is 99:1 to 55:45.

7. A pharmaceutical composition according to claim 6, wherein the pharmaceutical excipient yields a composition which can be administered by a route selected from the group consisting of intravenous, oral and transdermal.

8. A pharmaceutical composition according to claim 4, wherein the R:S ratio is 35:65.

9. A pharmaceutical composition according to claim 4, wherein the R:S ratio is 25:75.

10. A pharmaceutical composition according to claim 6, wherein the R:S ratio is 65:35.

11. A pharmaceutical composition according to claim 6, wherein the R:S ratio is 75:25.

12. A process of making a pharmaceutical composition containing R-verapamil and S-verapamil comprising adding unequal amounts of R-verapamil and S-verapamil to a pharmaceutical excipient the relative amounts of R- and S-verapamil being chosen to achieve a predetermined target plasma level or a predetermined pharmaceutical activity.

13. A process for preparing a pharmaceutical composition containing R-verapamil and S-verapamil comprising:
 a) selecting a pharmaceutical activity possessed by R-verapamil or S-verapamil, alone or in combination;
 b) determining a plasma target level of R-verapamil and S-verapamil which will achieve the desired pharmaceutical activity;
 c) selecting a dosage form for administering the R-verapamil and S-verapamil;
 d) determining the relative amounts of R- and S-verapamil to incorporate into the selected dosage form to achieve the target plasma level; and
 e) combining the relative amounts of R- and S-verapamil needed to achieve the target plasma level with one or more pharmaceutical excipients to prepare the selected dosage form.

14. A process according to claim 13, wherein the pharmaceutical activity is an antihypertensive effect.

15. A process according to claim 13, wherein the pharmaceutical activity is control of supraventricular tachycardia.

16. A process according to claim 13, wherein the pharmaceutical activity is treatment of angina.

17. A process according to claim 13, wherein the target plasma level of R-verapamil and S-verapamil is about 85:15.

18. A process according to claim 13, wherein the target plasma level of R-verapamil and S-verapamil is about 64:36.

19. A process according to claim 13, wherein the target plasma level of R-verapamil and S-verapamil is about 50:50.

20. A process according to claim 13, wherein the dosage form is selected from the group consisting of intravenous, oral-immediate release and oral-sustained release formulations.

* * * * *

UNITED STATES PATENT AND TRADEMARK OFFICE
CERTIFICATE OF CORRECTION

PATENT NO. : 5,955,500
DATED : September 21, 1999
INVENTOR(S) : JAMES A. LONGSTRETH ET AL.

It is certified that error appears in the above-identified patent and that said Letters Patent is hereby corrected as shown below:

COLUMN 2:

Line 58, "pressure," should read --pressure and--.

COLUMN 3:

Line 30, "ranges" should read --ranges,--.

COLUMN 4:

Line 61, "HFLC" should read --HPLC--.

COLUMN 5:

Line 3, "HFLC" should read --HPLC--; and
    Line 35, "are" should read --is--.

COLUMN 6:

Line 56, "after load" should read --afterload--.

UNITED STATES PATENT AND TRADEMARK OFFICE
CERTIFICATE OF CORRECTION

PATENT NO. : 5,955,500

DATED : September 21, 1999

INVENTOR(S) : JAMES A. LONGSTRETH ET AL.

It is certified that error appears in the above-identified patent and that said Letters Patent is hereby corrected as shown below:

COLUMN 10:

Line 24, "apparent," should read --apparent--.

COLUMN 12:

Line 5, "other-than" should read --other than--.

COLUMN 13:

Table 5, under "2 min":

$149\pm10\dagger\dagger\S\S$    $154\pm10\dagger\dagger\S\S$ and "80/205" should read --80/20S--.

COLUMN 14:

Table 6, under "4 min":
"100±3" should read --102±3--.

UNITED STATES PATENT AND TRADEMARK OFFICE
CERTIFICATE OF CORRECTION

PATENT NO.   : 5,955,500
DATED        : September 21, 1999
INVENTOR(S)  : JAMES A. LONGSTRETH ET AL.

It is certified that error appears in the above-identified patent and that said Letters Patent is hereby corrected as shown below:

COLUMN 17:

Table 8, "80/205" should read --80/20S-- and
      "20/805" should read --20/80S--.

COLUMN 19:

Line 30, "Repolarizadon" should read --Repolarization--.

COLUMN 20:

Line 63, ""Verapamil" should read --"Verapamil:--.

COLUMN 22:

Line 13, "invention," should read --invention--;
   Line 29, "water soluble" should read --water-soluble--;
   Line 42, "preferred" should read --prepared--; and
   Line 48, "preferred" should read --prepared--.

COLUMN 23:

Line 32, "a" should be deleted.

UNITED STATES PATENT AND TRADEMARK OFFICE
CERTIFICATE OF CORRECTION

PATENT NO. : 5,955,500
DATED : September 21, 1999
INVENTOR(S) : JAMES A. LONGSTRETH ET AL.

It is certified that error appears in the above-identified patent and that said Letters Patent is hereby corrected as shown below:

COLUMN 24:

Line 54, "with" should read --within--.

COLUMN 26:

Line 11, "excipient" should read --excipient,--; and
Line 46, "excipient" should read --excipient,--.

Signed and Sealed this

Fifth Day of December, 2000

Q. TODD DICKINSON

Attest:

Attesting Officer

Director of Patents and Trademarks